US008785385B2

(12) United States Patent
Stout et al.

(10) Patent No.: US 8,785,385 B2
(45) Date of Patent: Jul. 22, 2014

(54) RTEF-1 VARIANTS AND USES THEREOF

(75) Inventors: J. Timothy Stout, Portland, OR (US);
Binoy Appukuttan, Portland, OR (US);
Trevor McFarland, Portland, OR (US);
Anna Dye, Portland, OR (US)

(73) Assignees: Research Development Foundation, Carson City, NV (US); Oregon Health & Science University, Portland, OR (US)

( * ) Notice: Subject to any disclaimer, the term of this patent is extended or adjusted under 35 U.S.C. 154(b) by 151 days.

(21) Appl. No.: 13/089,687

(22) Filed: Apr. 19, 2011

(65) Prior Publication Data

US 2012/0063994 A1    Mar. 15, 2012

Related U.S. Application Data

(60) Provisional application No. 61/325,675, filed on Apr. 19, 2010.

(51) Int. Cl.
*C07K 14/435* (2006.01)
*A61K 38/00* (2006.01)
*A61K 38/16* (2006.01)
*A61K 38/17* (2006.01)

(52) U.S. Cl.
USPC .......... 514/13.3; 514/1.1; 514/21.2; 530/300; 530/350

(58) Field of Classification Search
None
See application file for complete search history.

(56) References Cited

U.S. PATENT DOCUMENTS

| | | | |
|---|---|---|---|
| 5,776,776 A | 7/1998 | Ordahl et al. | 438/366 |
| 5,994,136 A | 11/1999 | Naldini et al. | 435/455 |
| 6,013,516 A | 1/2000 | Verma et al. | 435/325 |
| 7,122,181 B2 | 10/2006 | Stout et al. | 424/93.2 |
| 7,183,388 B2 | 2/2007 | Denardo et al. | 530/387.3 |
| 2003/0008374 A1 | 1/2003 | Trono et al. | 435/235.1 |
| 2003/0082789 A1 | 5/2003 | Trono et al. | 435/235.1 |
| 2005/0175591 A1 | 8/2005 | Stout et al. | 424/93.2 |
| 2006/0223114 A1 | 10/2006 | Stemmer et al. | 435/7.1 |
| 2006/0234299 A1 | 10/2006 | Stemmer et al. | 435/7.1 |
| 2008/0138330 A1 | 6/2008 | Shie et al. | 424/130.1 |
| 2009/0117119 A1 | 5/2009 | Stout et al. | 514/12 |

FOREIGN PATENT DOCUMENTS

WO    WO 2005/034881    4/2005
WO    WO 2008/154351    12/2008

OTHER PUBLICATIONS

Appukuttan et al., "Identification of novel alternatively spliced isoforms of RTEF-1 within human ocular vascular endothelial cells and murine retina," *Investigative Ophthalmology & Visual Science*, 48 (8): 3775-3782, 2007.

Benottehan and Colombo, "Anti-angiogenic strategies for cancer therapy (Review)," *International Journal of Oncology*, 27:563-574, 2005.
Donahue et al., "Retinal vascular endothelial growth factor (VEGF) mRNA expression is altered in relation to neovascularization in oxygen induced retinopathy," *Curr. Eye Res.*, 15 (2): 175-184, 1996.
Eskens, "Angiogenesis inhibitors in clinical development; where are we now and where are we going?" *British Journal of Cancer*, 90:1-7, 2004.
Farrance et al., "The role of transcription enhancer factor-1 (TEF-1) related proteins in the formation of M-CAT binding complexes in muscle and non-muscle tissues," *J. Biol. Chem.*, 271 (14): 8266-8274, 1996.
Frigerio et al, "Analysis of 2166 clones from a human colorectal cancer cDNA library by partial sequencing," *Hum. Mol. Genet.*, 4 (1): 37-43. 1995.
Gragoudas et al., "Pegaptanib for neovascular age-related macular degeneration," *N. Engl. J. Med.*, 351 (27): 2805-2816, 2004.
Jiang et al., "Novel human TEF-1 isoforms exhibit altered DNA binding and functional properties," *Biochemistry*, 39 (12): 3505-3513, 2000.
Kanda et al., "Comparison of ICAM-1 and VCAM-1 expression in various human endothelial cell types and smooth muscle cells," *Endothelium*, 6 (1): 33-44. 1998.
Kaneko and DePamphilis, "Regulation of gene expression at the beginning of mammalian development and the TEAD family of transcription factors", *Dev. Genet.*, 22 (1): 43-55, 1998.
Kelleher and Vos, "Long-term episomal gene delivery in human lymphoid cells using human and avian adenoviral-assisted transfection," *Biotechniques*, 17 (6): 1110-1117, 1994.
Lashkari et al., "Vascular endothelial growth factor and hepatocyte growth factor levels are differentially elevated in patients with advanced retinopathy of prematurity," *Am. J. Pathol.*, 156 (4): 1337-1344, 2000.
Miller, "Vascular endothelial growth factor and ocular neovascularization", *Am. J. Pathol.* 151 (1): 13-23, 1997.
Neri and Bicknell, "Tumour vascular targeting," *Nat. Rev. Cancer*, 5(6):436-446, 2005.
Ngo et al., "Computational complexity, protein structure prediction, and the Levinthal paradox," In: *The Protein Folding Problem and Tertiary Structure Prediction*, Merz and Le Grand, Eds. Birkhauser: Boston, pp. 491-495, 1994.
Office Communication issued in U.S. Appl. No. 12/134,626, dated Feb. 2, 2011.

(Continued)

*Primary Examiner* — Christine J Saoud
*Assistant Examiner* — Jon M Lockhardt
(74) *Attorney, Agent, or Firm* — Parker Highlander PLLC

(57) ABSTRACT

Disclosed are variant RTEF-1 polypeptides having an RTEF-1 amino acid sequence with one or more internal deletions, wherein the polypeptides reduce VEGF promoter activity. Some of the RTEF-1 polypeptides include an amino acid sequence that is at least 80% identical to the contiguous amino acids of 1) amino acids 24 to 47 of SEQ ID NO:15 and 2) each of SEQ ID NOs:16 and 17, but does not comprise the contiguous amino acids of SEQ ID NOs:8, 9, 11, or 12. Also disclosed are nucleic acids encoding the variant RTEF-1 polypeptides of the present invention. Pharmaceutical compositions that include the polypeptides and nucleic acids of the present invention are also disclosed. Methods of inducing cell contact inhibition, regulating organ size, and reducing intracellular YAP activity are also set forth, as well as methods of treating hyperproliferative diseases such as cancer using the pharmaceutical compositions of the present invention.

39 Claims, 5 Drawing Sheets

(56) References Cited

OTHER PUBLICATIONS

Office Communication issued in U.S. Appl. No. 12/134,626, dated Mar. 28, 2011.
Office Communication issued in U.S. Appl. No. 12/134,626, dated Oct. 7, 2011.
Office Communication issued in U.S. Appl. No. 12/134,626, dated Jan. 11, 2012.
Office Communication issued in U.S. Appl. No. 12/134,626, dated Oct. 24, 2012.
Onda et al., "In vitro and in vivo cytotoxic activities of recombinant immunotoxin 8H9(Fv)-PE38 against breast cancer, osteosarcoma, and neuroblastoma," Cancer Res., 64 (4): 1419-1424, 2004.
PCT International Preliminary Report on Patentability issued in International application No. PCT/US2011/032994, dated May 11, 2012.
PCT International Search Report and Written Opinion issued in International application No. PCT/US2011/032994, dated Jul. 6, 2011.
PCT international Search Report and Written Opinion, issued in International application No. PCT/US2008/066058, dated Sep. 5, 2008.
PCT Written Opinion of the International Preliminary Examining Authority issued in International application No. PCT/US2011-032994, dated Mar. 30, 2012.
Pe'er et al., "Hypoxia-induced expression of vascular endothelial growth factor by retinal cells is a common factor in neovascularizing ocular diseases," Lab. Invest., 72 (6): 638-645, 1995.
Pettit and Gombotz, "The development of site-specific drug-delivery systems for protein and peptide biopharmaceuticals," Trends Biotechnol., 16(8):343-349, 1998.
Pierce et al., "Regulation of vascular endothelial growth factor by oxygen in a model of retinopathy of prematurity," Arch. Ophthahnol., 114 (10):1219-1228, 1996.
Rothbard et al., "Conjugation of arginine oligomers to cyclosporin A facilitates topical delivery and inhibition of inflammation," Nat. Medicine, 6 (11): 1253-1257, 2000.
Shie et al., "RTEF1, a novel transcriptional stimulator of endothelial growth factor in hypoxic endothelial cells," J. of Biol. Chem., 279 (24): 25010-25016, 2004.
Shimizu et al. "Antinoevascular therapy, a novel antiangiogenic approach," Expert Opin. Ther. Targets, 9(1):63-76, 2005.
Silverman et al., "Differential E-selectin expression by iris versus retina microvascular endothelial cells cultured from the same individuals," Microvasc. Res., 70 (1-2): 32-42, 2005.
Skolnick et al., "From genes to protein structure and function: novel applications of computational approaches in the genomic era," Trends in Biotech., 19(1):34-39, 2000.
Stewart et al., "Cloning of human RTEF-1, a transcriptional enhancer factor-1-related gene preferentially expressed in skeletal muscle: evidence for an ancient multigene family," Genomics, 37 (1): 68-76, 1996.
Sweeney et al., "Resistance in the anti-angiogenic era: nay-saying or word of caution," TRENDS in Molecular Medicine, 9(1):24-29, 2003.
Uniprot: "Sequence UPI0000488889," Dec. 1, 2004. XP55022924, retrieved on Mar. 26, 2012.
Unirprot: "Sequence UPI0000E001FC," Sep. 13, 2006, XP55022838, Retrieved from the Internet: www.uniprot.org/uniparc/UPI0000E001FC, retrieved on Mar. 26, 2012.
Vannay et al., "Association of genetic polymorphisms of vascular endothelial growth factor and risk for proliferative retinopathy of prematurity," Pediatr. Res., 57 (3): 396-398, 2005.
Von Minckwitz et al., "Phase I clinical study of the recombinant antibody toxin scFv(FRP5)-ETA specific for the ErbB2/HER2 receptor in patients with advanced solid malignomas." Breast Cancer Res., 7 (5): R616-626, 2005.
Wells et al., "Additivity of mutational effects in proteins," Biotechnology, 29(37):8509-8517, 1990.
Winthrop et al.,"Selection and characterization or anti-MUC-1 scFvs intended for targeted therapy," Clin. Cancer Res., 9 (10 pt. 2): 3845s-3853s, 2003.
Wright et al., "Guanidinium rich peptide transporters and drug delivery," Curr. Protein Pept. Sci., 4 (2): 105-124, 2003.
Yasunami et al., "A novel family of TEA domain-containing transcription factors with distinct spatiotemporal expression patterns," Biochem. Biohpys. Res. Commun., 228 (2): 364-370, 1996.
Yockey et al.. "cDNA cloning and characterization of murine transcriptional enhancer factor-1-related protein 1, a transcription factor that binds to the M-CAT motif," J. of Biol. Chem., 271 (7): 3727-3736, 1996.
Young et al., "Histopathology and vascular endothelial growth factor in untreated and diode laser-treated retinopathy of prematurity," J. Aapos., 1 (2): 105-110, 1997.
Zeng and Hong, "The emerging role of the Hippo pathway in cell contact inhibition, organ size control, and cancer development in mammals," Cancer Cell, 13:188-192, 2008.
Zuzarte et al., "Tumor cell splice variants of the transcription factor TEF-1 induced by SV40 T-antigen transformation," Biochim. Biophys. Acta., 1517 (1): 82-90. 2000.

FIGs. 1A-C
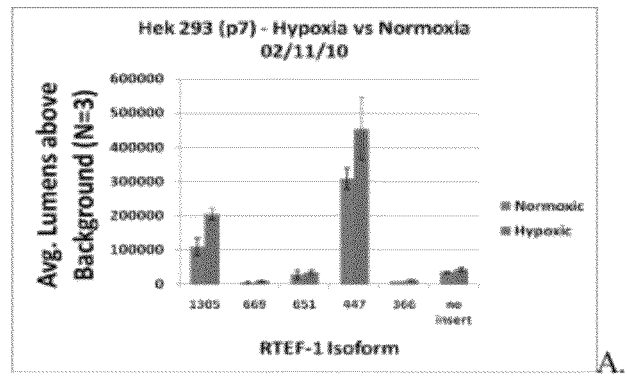
A.
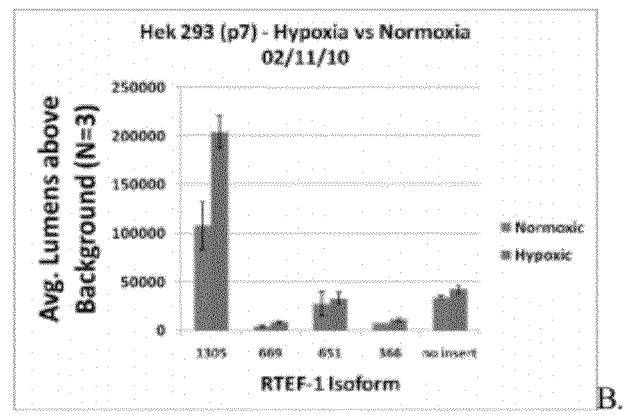
B.
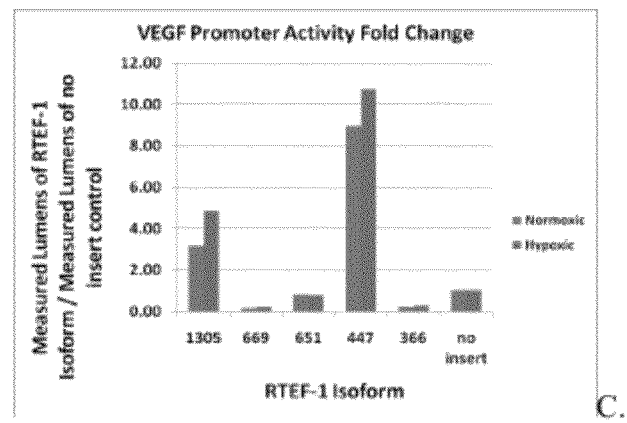
C.

A

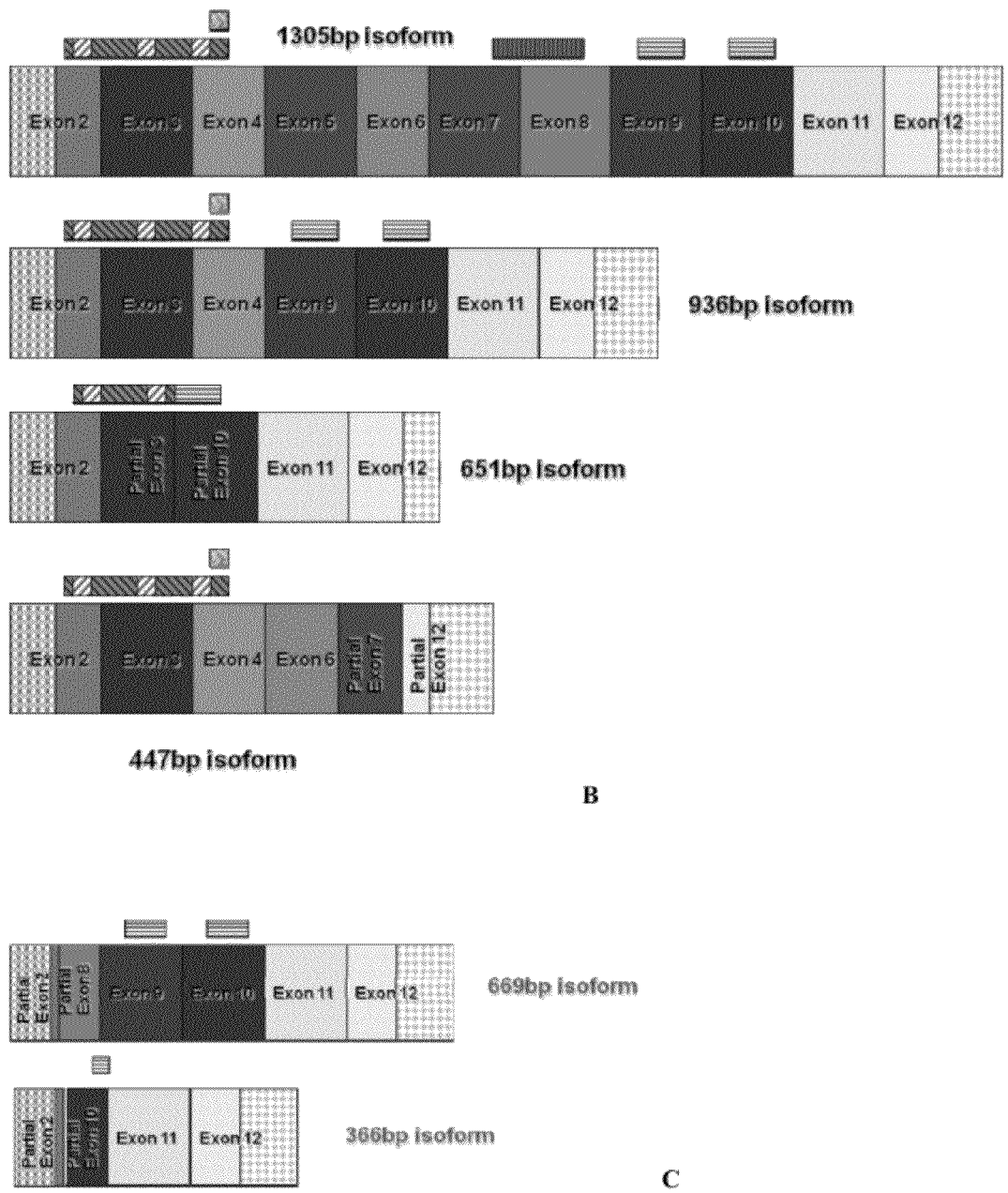
FIGs. 2B-C

FIG. 3.

MEGTAGTITSNEWSSPTSPEGSTASGGSQALDKPIDNDAEGVWSPDIEQSF
QEALAIYPPCGRRKIILSDEGKMYGRNELIARYIKLRTGKTRTRKQVSSHI
QVLARRKAREIQAKLKDQAAKDKALQSMAAMSSAQIISATAFHSSMALARG
PGRPAVSGFWQGALPGQAGTSHDVKPFSQQTYAVQPPLPLPGFESPAGPAP
SPSAPPAPPWQGRSVASSKLWMLEFSAFLEQQQDPDTYNKHLFVHIGQSSP
SYSDPYLEAVDIRQIYDKFPEKKGGLKDLFERGPSNAFFLVKFWADLNTNI
EDEGSSFYGVSSQYESPENMIITCSTKVCSFGKQVVEKVETEYARYENGHY
SYRIHRSPLCEYMINFIHKLKHLPEKYMMNSVLENFTILQVVTNRDTQETL
LCIAYVFEVSASEHGAQHHIYRLVKE

FIG. 4.

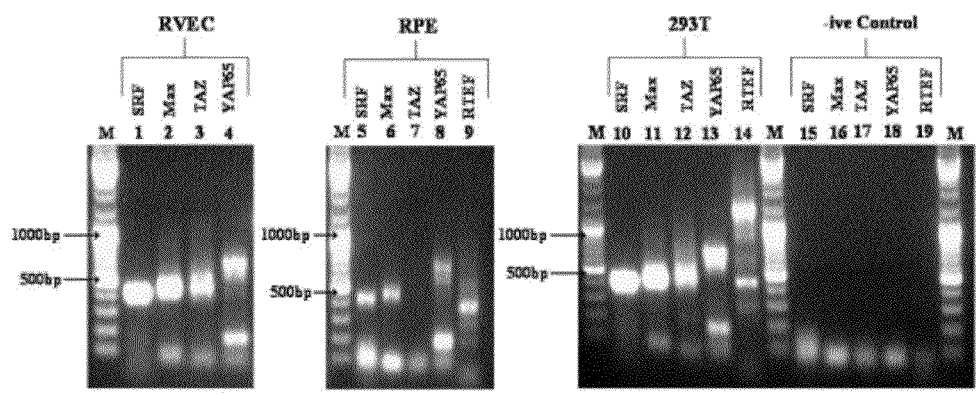

SEQUENCE LISTING

```
<160> NUMBER OF SEQ ID NOS: 23

<210> SEQ ID NO 1
<211> LENGTH: 222
<212> TYPE: PRT
<213> ORGANISM: Homo sapiens

<400> SEQUENCE: 1

Met Glu Gly Thr Ala Gly Thr Ile Thr Ser Lys Leu Trp Met Leu Glu
1               5                   10                  15

Phe Ser Ala Phe Leu Glu Gln Gln Gln Asp Pro Asp Thr Tyr Asn Lys
            20                  25                  30

His Leu Phe Val His Ile Gly Gln Ser Ser Pro Ser Tyr Ser Asp Pro
        35                  40                  45

Tyr Leu Glu Ala Val Asp Ile Arg Gln Ile Tyr Asp Lys Phe Pro Glu
    50                  55                  60

Lys Lys Gly Gly Leu Lys Asp Leu Phe Glu Arg Gly Pro Ser Asn Ala
65                  70                  75                  80

Phe Phe Leu Val Lys Phe Trp Ala Asp Leu Asn Thr Asn Ile Glu Asp
                85                  90                  95

Glu Gly Ser Ser Phe Tyr Gly Val Ser Ser Gln Tyr Glu Ser Pro Glu
            100                 105                 110

Asn Met Ile Ile Thr Cys Ser Thr Lys Val Cys Ser Phe Gly Lys Gln
        115                 120                 125

Val Val Glu Lys Val Glu Thr Glu Tyr Ala Arg Tyr Glu Asn Gly His
    130                 135                 140

Tyr Ser Tyr Arg Ile His Arg Ser Pro Leu Cys Glu Tyr Met Ile Asn
145                 150                 155                 160

Phe Ile His Lys Leu Lys His Leu Pro Glu Lys Tyr Met Met Asn Ser
                165                 170                 175

Val Leu Glu Asn Phe Thr Ile Leu Gln Val Val Thr Asn Arg Asp Thr
            180                 185                 190

Gln Glu Thr Leu Leu Cys Ile Ala Tyr Val Phe Glu Val Ser Ala Ser
        195                 200                 205

Glu His Gly Ala Gln His His Ile Tyr Arg Leu Val Lys Glu
    210                 215                 220

<210> SEQ ID NO 2
<211> LENGTH: 121
<212> TYPE: PRT
<213> ORGANISM: Homo sapiens

<400> SEQUENCE: 2

Met Glu Gly Thr Ala Gly Thr Ile Thr Pro Glu Asn Met Ile Ile Thr
```

```
1               5               10              15
Cys Ser Thr Lys Val Cys Ser Phe Gly Lys Gln Val Glu Lys Val
                20              25              30

Glu Thr Glu Tyr Ala Arg Tyr Glu Asn Gly His Tyr Ser Tyr Arg Ile
                35              40              45

His Arg Ser Pro Leu Cys Glu Tyr Met Ile Asn Phe Ile His Lys Leu
        50              55              60

Lys His Leu Pro Glu Lys Tyr Met Met Asn Ser Val Leu Glu Asn Phe
65              70              75              80

Thr Ile Leu Gln Val Val Thr Asn Arg Asp Thr Gln Glu Thr Leu Leu
                85              90              95

Cys Ile Ala Tyr Val Phe Glu Val Ser Ala Ser Glu His Gly Ala Gln
                100             105             110

His His Ile Tyr Arg Leu Val Lys Glu
                115             120

<210> SEQ ID NO 3
<211> LENGTH: 434
<212> TYPE: PRT
<213> ORGANISM: Homo sapiens

<400> SEQUENCE: 3

Met Glu Gly Thr Ala Gly Thr Ile Thr Ser Asn Glu Trp Ser Ser Pro
1               5               10              15

Thr Ser Pro Glu Gly Ser Thr Ala Ser Gly Gly Ser Gln Ala Leu Asp
                20              25              30

Lys Pro Ile Asp Asn Asp Ala Glu Gly Val Trp Ser Pro Asp Ile Glu
                35              40              45

Gln Ser Phe Gln Glu Ala Leu Ala Ile Tyr Pro Pro Cys Gly Arg Arg
        50              55              60

Lys Ile Ile Leu Ser Asp Glu Gly Lys Met Tyr Gly Arg Asn Glu Leu
65              70              75              80

Ile Ala Arg Tyr Ile Lys Leu Arg Thr Gly Lys Thr Arg Thr Arg Lys
                85              90              95

Gln Val Ser Ser His Ile Gln Val Leu Ala Arg Arg Lys Ala Arg Glu
                100             105             110

Ile Gln Ala Lys Leu Lys Asp Gln Ala Ala Lys Asp Lys Ala Leu Gln
                115             120             125

Ser Met Ala Ala Met Ser Ser Ala Gln Ile Ile Ser Ala Thr Ala Phe
        130             135             140

His Ser Ser Met Ala Leu Ala Arg Gly Pro Gly Arg Pro Ala Val Ser
145             150             155             160

Gly Phe Trp Gln Gly Ala Leu Pro Gly Gln Ala Gly Thr Ser His Asp
                165             170             175

Val Lys Pro Phe Ser Gln Gln Thr Tyr Ala Val Gln Pro Pro Leu Pro
                180             185             190

Leu Pro Gly Phe Glu Ser Pro Ala Gly Pro Ala Pro Ser Pro Ser Ala
                195             200             205

Pro Pro Ala Pro Pro Trp Gln Gly Arg Ser Val Ala Ser Ser Lys Leu
        210             215             220

Trp Met Leu Glu Phe Ser Ala Phe Leu Glu Gln Gln Asp Pro Asp
225             230             235             240

Thr Tyr Asn Lys His Leu Phe Val His Ile Gly Gln Ser Ser Pro Ser
                245             250             255
```

-continued

```
Tyr Ser Asp Pro Tyr Leu Glu Ala Val Asp Ile Arg Gln Ile Tyr Asp
            260                 265                 270

Lys Phe Pro Glu Lys Lys Gly Gly Leu Lys Asp Leu Phe Glu Arg Gly
        275                 280                 285

Pro Ser Asn Ala Phe Phe Leu Val Lys Phe Trp Ala Asp Leu Asn Thr
    290                 295                 300

Asn Ile Glu Asp Glu Gly Ser Ser Phe Tyr Gly Val Ser Ser Gln Tyr
305                 310                 315                 320

Glu Ser Pro Glu Asn Met Ile Ile Thr Cys Ser Thr Lys Val Cys Ser
                325                 330                 335

Phe Gly Lys Gln Val Val Glu Lys Val Glu Thr Glu Tyr Ala Arg Tyr
            340                 345                 350

Glu Asn Gly His Tyr Ser Tyr Arg Ile His Arg Ser Pro Leu Cys Glu
        355                 360                 365

Tyr Met Ile Asn Phe Ile His Lys Leu Lys His Leu Pro Glu Lys Tyr
    370                 375                 380

Met Met Asn Ser Val Leu Glu Asn Phe Thr Ile Leu Gln Val Val Thr
385                 390                 395                 400

Asn Arg Asp Thr Gln Glu Thr Leu Leu Cys Ile Ala Tyr Val Phe Glu
                405                 410                 415

Val Ser Ala Ser Glu His Gly Ala Gln His His Ile Tyr Arg Leu Val
            420                 425                 430

Lys Glu

<210> SEQ ID NO 4
<211> LENGTH: 311
<212> TYPE: PRT
<213> ORGANISM: Homo sapiens

<400> SEQUENCE: 4

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Ala Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Tyr Asn Lys His Leu Phe Val His Ile Gly
        115                 120                 125

Gln Ser Ser Pro Ser Tyr Ser Asp Pro Tyr Leu Glu Ala Val Asp Ile
    130                 135                 140

Arg Gln Ile Tyr Asp Lys Phe Pro Glu Lys Lys Gly Gly Leu Lys Asp
145                 150                 155                 160

Leu Phe Glu Arg Gly Pro Ser Asn Ala Phe Phe Leu Val Lys Phe Trp
                165                 170                 175

Ala Asp Leu Asn Thr Asn Ile Glu Asp Glu Gly Ser Ser Phe Tyr Gly
            180                 185                 190
```

```
Val Ser Ser Gln Tyr Glu Ser Pro Glu Asn Met Ile Ile Thr Cys Ser
        195                 200                 205

Thr Lys Val Cys Ser Phe Gly Lys Gln Val Val Glu Lys Val Glu Thr
210                 215                 220

Glu Tyr Ala Arg Tyr Glu Asn Gly His Tyr Ser Tyr Arg Ile His Arg
225                 230                 235                 240

Ser Pro Leu Cys Glu Tyr Met Ile Asn Phe Ile His Lys Leu Lys His
                245                 250                 255

Leu Pro Glu Lys Tyr Met Met Asn Ser Val Leu Glu Asn Phe Thr Ile
                260                 265                 270

Leu Gln Val Val Thr Asn Arg Asp Thr Gln Glu Thr Leu Leu Cys Ile
            275                 280                 285

Ala Tyr Val Phe Glu Val Ser Ala Ser Glu His Gly Ala Gln His His
        290                 295                 300

Ile Tyr Arg Leu Val Lys Glu
305                 310

<210> SEQ ID NO 5
<211> LENGTH: 216
<212> TYPE: PRT
<213> ORGANISM: Homo sapiens

<400> SEQUENCE: 5

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
                20                  25                  30

Lys Pro Ile Asp Asn Asp Ala Glu Gly Val Trp Ser Pro Asp Ile Glu
            35                  40                  45

Gln Ser Phe Gln Glu Ala Leu Ala Ile Tyr Pro Pro Cys Gly Arg Arg
        50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Ser Ser Phe Tyr
                85                  90                  95

Gly Val Ser Ser Gln Tyr Glu Ser Pro Glu Asn Met Ile Ile Thr Cys
            100                 105                 110

Ser Thr Lys Val Cys Ser Phe Gly Lys Gln Val Val Glu Lys Val Glu
        115                 120                 125

Thr Glu Tyr Ala Arg Tyr Glu Asn Gly His Tyr Ser Tyr Arg Ile His
    130                 135                 140

Arg Ser Pro Leu Cys Glu Tyr Met Ile Asn Phe Ile His Lys Leu Lys
145                 150                 155                 160

His Leu Pro Glu Lys Tyr Met Met Asn Ser Val Leu Glu Asn Phe Thr
                165                 170                 175

Ile Leu Gln Val Val Thr Asn Arg Asp Thr Gln Glu Thr Leu Leu Cys
            180                 185                 190

Ile Ala Tyr Val Phe Glu Val Ser Ala Ser Glu His Gly Ala Gln His
        195                 200                 205

His Ile Tyr Arg Leu Val Lys Glu
    210                 215

<210> SEQ ID NO 6
<211> LENGTH: 148
<212> TYPE: PRT
<213> ORGANISM: Homo sapiens
```

```
<400> SEQUENCE: 6

Met Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Gly Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly Arg Asn Glu Leu
65                  70                  75                  80

Ile Ala Arg Tyr Ile Lys Leu Arg Thr Gly Lys Thr Arg Thr Arg Lys
                85                  90                  95

Gln Val Ser Ser His Ile Gln Val Leu Ala Arg Arg Lys Ala Arg Glu
            100                 105                 110

Ile Gln Ala Lys Leu Lys Phe Trp Gln Gly Ala Leu Pro Gly Gln Ala
        115                 120                 125

Glu Thr Ser His Asp Val Lys Pro Phe Ser Gln His His Ile Tyr Arg
    130                 135                 140

Leu Val Lys Glu
145

<210> SEQ ID NO 7
<211> LENGTH: 76
<212> TYPE: PRT
<213> ORGANISM: Artificial Sequence
<220> FEATURE:
<223> OTHER INFORMATION: Synthetic peptide

<400> SEQUENCE: 7

Leu Glu Gly Thr Ala Gly Thr Ile Thr Ser Asn Glu Trp Ser Ser Pro
1               5                   10                  15

Thr Ser Pro Glu Gly Ser Thr Ala Ser Gly Gly Ser Gln Ala Leu Asp
            20                  25                  30

Lys Pro Ile Asp Asn Asp Ala Glu Gly Val Trp Ser Pro Asp Ile Glu
        35                  40                  45

Gln Ser Phe Gln Glu Ala Leu Ala Ile Tyr Pro Pro Cys Gly Arg Arg
    50                  55                  60

Lys Ile Ile Leu Ser Asp Glu Gly Lys Met Tyr Gly
65                  70                  75

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide

<400> SEQUENCE: 8

Arg Asn Glu Leu Ile Ala Arg Tyr Ile Lys Leu Arg Thr Gly Lys Thr
1               5                   10                  15

Arg Thr Arg Lys Gln
            20

<210> SEQ ID NO 9
<211> LENGTH: 21
<212> TYPE: PRT
<213> ORGANISM: Artificial Sequence
```

```
<220> FEATURE:
<223> OTHER INFORMATION: Synthetic peptide

<400> SEQUENCE: 9

Val Ser Ser His Ile Gln Val Leu Ala Arg Arg Lys Ala Arg Glu Ile
1               5                   10                  15

Gln Ala Lys Leu Lys
            20

<210> SEQ ID NO 10
<211> LENGTH: 43
<212> TYPE: PRT
<213> ORGANISM: Artificial Sequence
<220> FEATURE:
<223> OTHER INFORMATION: Synthetic peptide

<400> SEQUENCE: 10

Asp Gln Ala Ala Lys Asp Lys Ala Leu Gln Ser Met Ala Ala Met Ser
1               5                   10                  15

Ser Ala Gln Ile Ile Ser Ala Thr Ala Phe His Ser Ser Met Ala Leu
            20                  25                  30

Ala Arg Gly Pro Gly Arg Pro Ala Val Ser Gly
        35                  40

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Phe Trp Gln Gly Ala Leu Pro Gly Gln Ala Gly Thr Ser His Asp
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Val Lys Pro Phe Ser Gln Gln Thr Tyr Ala Val Gln Pro Pro Leu Pro
1               5                   10                  15

Leu Pro Gly

<210> SEQ ID NO 13
<211> LENGTH: 46
<212> TYPE: PRT
<213> ORGANISM: Artificial Sequence
<220> FEATURE:
<223> OTHER INFORMATION: Synthetic peptide

<400> SEQUENCE: 13

Phe Glu Ser Pro Ala Gly Pro Ala Pro Ser Pro Ser Ala Pro Pro Ala
1               5                   10                  15

Pro Pro Trp Gln Gly Arg Ser Val Ala Ser Ser Lys Leu Trp Met Leu
            20                  25                  30

Glu Phe Ser Ala Phe Leu Glu Gln Gln Gln Asp Pro Asp Thr
        35                  40                  45

<210> SEQ ID NO 14
```

```
<211> LENGTH: 58
<212> TYPE: PRT
<213> ORGANISM: Artificial Sequence
<220> FEATURE:
<223> OTHER INFORMATION: Synthetic peptide

<400> SEQUENCE: 14

Tyr Asn Lys His Leu Phe Val His Ile Gly Gln Ser Ser Pro Ser Tyr
1               5                   10                  15

Ser Asp Pro Tyr Leu Glu Ala Val Asp Ile Arg Gln Ile Tyr Asp Lys
            20                  25                  30

Phe Pro Glu Lys Lys Gly Gly Leu Lys Asp Leu Phe Glu Arg Gly Pro
        35                  40                  45

Ser Asn Ala Phe Phe Leu Val Lys Phe Trp
    50                  55

<210> SEQ ID NO 15
<211> LENGTH: 47
<212> TYPE: PRT
<213> ORGANISM: Artificial Sequence
<220> FEATURE:
<223> OTHER INFORMATION: Synthetic peptide

<400> SEQUENCE: 15

Ala Asp Leu Asn Thr Asn Ile Glu Asp Glu Gly Ser Ser Phe Tyr Gly
1               5                   10                  15

Val Ser Ser Gln Tyr Glu Ser Pro Glu Asn Met Ile Ile Thr Cys Ser
            20                  25                  30

Thr Lys Val Cys Ser Phe Gly Lys Gln Val Val Glu Lys Val Glu
        35                  40                  45

<210> SEQ ID NO 16
<211> LENGTH: 51
<212> TYPE: PRT
<213> ORGANISM: Artificial Sequence
<220> FEATURE:
<223> OTHER INFORMATION: Synthetic peptide

<400> SEQUENCE: 16

Thr Glu Tyr Ala Arg Tyr Glu Asn Gly His Tyr Ser Tyr Arg Ile His
1               5                   10                  15

Arg Ser Pro Leu Cys Glu Tyr Met Ile Asn Phe Ile His Lys Leu Lys
            20                  25                  30

His Leu Pro Glu Lys Tyr Met Met Asn Ser Val Leu Glu Asn Phe Thr
        35                  40                  45

Ile Leu Gln
    50

<210> SEQ ID NO 17
<211> LENGTH: 37
<212> TYPE: PRT
<213> ORGANISM: Artificial Sequence
<220> FEATURE:
<223> OTHER INFORMATION: Synthetic peptide

<400> SEQUENCE: 17

Val Val Thr Asn Arg Asp Thr Gln Glu Thr Leu Leu Cys Ile Ala Tyr
1               5                   10                  15

Val Phe Glu Val Ser Ala Ser Glu His Gly Ala Gln His His Ile Tyr
            20                  25                  30

Arg Leu Val Lys Glu
        35
```

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Pro Pro Lys Lys Lys Arg Lys Val
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Arg Arg Met Lys Trp Lys Lys
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Arg Met Arg Arg Met Arg Arg Met Arg Arg
1               5                   10

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
tgtttcagcc gcagcctctc                                           20

<210> SEQ ID NO 22
<211> LENGTH: 18
<212> TYPE: DNA
<213> ORGANISM: Artificial Sequence
<220> FEATURE:
<223> OTHER INFORMATION: Synthetic primer

<400> SEQUENCE: 22
tgggggctgc ttcactgg                                             18

<210> SEQ ID NO 23
<211> LENGTH: 20
<212> TYPE: PRT
<213> ORGANISM: Homo sapiens

<400> SEQUENCE: 23

Met Tyr Arg Met Gln Leu Leu Ser Cys Ile Ala Leu Ser Leu Ala Leu
1               5                   10                  15

Val Thr Asn Ser
            20

RTEF-1 VARIANTS AND USES THEREOF

This application claims the benefit of U.S. Provisional Application No. 61/325,675 filed Apr. 19, 2010, which is incorporated herein by reference in its entirety.

The invention was made with government support under Grant No. NEI/NIH 1R01EY019042-01A1 awarded by the National Institutes of Health. The government has certain rights in the invention.

BACKGROUND OF THE INVENTION

1. Field of the Invention

The invention concerns the fields of molecular biology, cell biology, clinical medicine, pharmacotherapy, and oncology.

2. Description of Related Art

Transcriptional enhancer factor 1-related (RTEF-1) gene is a member of the TEA DNA binding domain gene family. The TEA DNA binding domain gene family is highly conserved from *Aspergillus nidulans*, yeast, *Drosophila*, mice to human. The TEA DNA binding family of proteins can be involved in both activation and repression of different genes and their particular function can be modified by association with other proteins (Kaneko & DePamphilis, 1998). Expression of specific members of these genes has been identified in various mammalian tissues, including heart, skeletal muscle, pancreas, placenta, brain and lung (Stewart et al., 1996; Yasunami et al., 1996; Farrance et al., 1996). Isoforms arising from alternative splicing of mRNA from a single gene, for transcriptional enhancer factor-1 (TEF-1) have been identified within a single tissue such as the pancreas (Zuzarte et al., 2000; Jiang et al., 2000). The expression profile of these genes within the mammalian eye has not been reported.

Transcripts of the RTEF-1 gene were first identified in chicken tissue and demonstrated to be enriched in cardiac and skeletal muscle (Farrance et al., 1996). The chicken RTEF-1 binds to the myocyte-specific CAT (M-CAT) cis DNA elements and regulates expression of muscle specific genes, and requires muscle specific cofactors for full transcriptional activation. Random screening of 2166 human colorectal cancer cDNA library identified a partial cDNA RTEF-1 sequence which lead to the isolation of a full length human homolog of the avian RTEF-1 from a heart cDNA library (Stewart et al., 1996; Frigerio et al., 1995). Northern blot analysis of human tissue indicated highest levels of expression in skeletal muscle and pancreas, with lower levels in heart, kidney and placenta, whereas message was not detected in liver, lung or brain (Stewart et al., 1996). Northern blot analysis of the mouse homolog of RTEF-1 indicates a different tissue expression pattern when compared to human. Adult mouse lung tissue expressed the highest level, with very low levels in kidney, heart and skeletal muscle and undetectable amounts in liver, thymus, spleen and brain, whereas RTEF-1 message was abundant in mouse embryonic skeletal muscle (Yockey et al., 1996). An alternatively spliced mouse isoform of RTEF-1 that lacks exon 5 when compare to the full length gene has been identified in mouse skeletal muscle cells (Yockey et al., 1996).

RTEF-1/TEAD4 has been shown to bind with Yes-associated protein (YAP) and modulate gene expression (Vassilev et al., 2001). Interacting at the end of the Hippo Pathway, TEAD and YAP control organ size during development and, thus, play an important role in the coordination of cell growth, proliferation, and apoptosis (Ota and Sasaki, 2008). Studies have shown that cell to cell interactions elicit signals though the Hippo Pathway which govern YAP-dependent RTEF-1/TEAD4 transcriptional activity (Nishioka et al., 2009). Disruption of the Hippo Pathway or altered activity of YAP (expression or localization) can lead to cell overgrowth and survival (Zeng and Hong, 2008). The four human TEAD proteins share more than 72% homology. Variable regions are found in the proline-rich domain and the n-terminus. The n-terminus is thought to be a target for phosphorylation whereas the c-terminus has been shown to bind with YAP. YAP binds to all four TEAD proteins (Vassilev et al., 2001).

YAP is found to be over expressed and diffuse in many tumors. YAP location and degree of overexpression varies between cancer types (Steinhardt et al., 2008). Wnt and Akt/PKB are two other pathways that are tightly regulated during development and seem to play large roles in tumor malignancy. Reduction of over expressed YAP activity is thought to be correlated with decreased cell migration, decreased Akt activation, and increased E-cadherin levels. Studies have shown that 50-80% of metastatic cancers express less E-cadherin compared to normal tissues (Orsulic et al., 1999) and YAP overexpression is found in many highly metastatic cancers that are associated with short survival (Wang et al., 2010). Immunoblotting suggests that E-cadherin and occludin levels decrease while N-cadherin, fibronectin, and Akt phosphorylation increase in the presence of YAP (Overholtzer et al., 2006). Likewise, YAP S94A mutation (abolishes YAP and TEAD4 interaction) results in an increase in E-cadherin and gamma-Catenin expression while N-cadherin and fibronectin level decrease (Zhao et al., 2008). Some studies have shown that tumor cells will revert to a benign phenotype upon E-cadherin re-establishment. E-cadherin/B-catenin complex is essential for cell adhesion. A decrease in E-cadherin results in an increase of free B-catenin, which can enter the nucleus and activate target genes which leads to cancer (Wnt pathway) (Semb and Christofori, 1998).

Balancing cell proliferation and apoptosis is essential for proper tissue growth, development, and function. Disruption can lead to excessive tissue loss with subsequence loss of function as in the case of excessive apoptosis or uncontrolled cell proliferation. The Hippo pathway is a potent regulator of tissue homeostasis by controlling cell growth, division, and apoptosis. The potent effect of YAP on cell growth, division, and apoptosis supports the notion that YAP functions as to maintain tissue homeostasis. Once dysregulated, it can lead to a malignant phenotype. Malignant cells might produce excess YAP during genomic amplification that might overwhelm the normal physiologic regulatory systems and result in abnormal cytoplasmic accumulation. Accumulation of YAP within the cytoplasm maintains a constant pool of the protein for nuclear translocation. The stability of YAP may be altered in neoplastic tissues resulting in ineffective protein turnover and excessive YAP activity.

Vascular endothelial growth factor (VEGF) is one proangiogenic factor that is known to be up regulated in retinal tissue under hypoxic conditions (Young et al., 1997; Pierce et al., 1996; Donahue et al., 1996; Pe'er et al., 1995). Recently the full length RTEF-1 protein has been identified to not only bind to the VEGF promoter but also to up-regulate the expression of VEGF, for instance under hypoxic conditions in bovine aortic endothelial cells (BAEC) (Shie et al., 2004). Microarray analysis revealed that RTEF-1 expression was up-regulated by 3-fold in BAEC under hypoxic conditions. Surprisingly, RTEF-1 mediated VEGF gene activation via interaction with Sp1 elements within the VEGF promoter and not M-CAT motifs. In addition RTEF mediated expression of VEGF is achieved independently of the hypoxia-inducible factor (HIF-1) and hypoxia responsive element (HRE) pathway of activation (Shie et al., 2004).

VEGF over-expression has been implicated in a variety of angiogenic disorders such as tumor angiogenesis and aberrant neovascularization. For example, it is well established that VEGF plays an important role in the development and severity of retinopathy of prematurity (ROP) and other ocular neovascular diseases (Lashkari et al., 2000; Miller, 1997; Vannay et al., 2005; Young et al., 1997). Given the prominent role of VEGF in such disorders a number of therapeutic strategies for inhibiting VEGF activity have been developed. However, current VEGF blockade therapies typically involve inhibiting the interaction of extra cellular VEGF with cognate cell surface receptors. Thus, there is a need for alternative strategies for VEGF blockade such as method for inhibiting VEGF production.

SUMMARY OF THE INVENTION

The present invention is in part based on the identification of splice variants of RTEF-1 that are particularly effective at reducing VEGF production. The enhancer isoforms (447 and 1305) are believed to be capable of binding the VEGF promoter to regulate gene expression whereas the inhibitor isoforms (651, ss651RMR, 366 and 669 and modifications of these isoforms), that usually lack a nuclear localization signal, repress VEGF production at the cellular level resulting in lower levels of secreted $VEGF_{165}$.

Given the prominent role of VEGF in a wide variety of diseases, such as cancer and other diseases associated with vascular proliferation, these RTEF-1 variants represent a new subset of therapeutic agents. The RTEF-1 variants of the present invention are also believed to be effective in reducing YAP activity in cells that overexpress or have elected YAP activity, such as certain cancer cells. The RTEF-1 variants of the present invention can thus be applied in regulating the amount of active YAP in the cytoplasm or nucleus of target cells, thus regulating cell growth and proliferation.

Certain embodiments of the present invention include isolated variant RTEF-1 isoforms that include one or more internal deletions, wherein the isoforms lacks a nuclear translation signal. The result is that the RTEF-1 variant remains confined to the cytoplasm of cells.

Some particular embodiments of the RTEF-1 isoforms of the present invention include an amino acid sequence that is at least 80% identical to the contiguous amino acids of 1) amino acids 24 to 47 of SEQ ID NO:15 (the amino acids encoded by exon 10) and 2) each of SEQ ID NO:16 (amino acids encoded by exon 11) and SEQ ID NO:17 (amino acids encoded by exon 12), but does not comprise the contiguous amino acids of SEQ ID NO:8 (amino acids encoded by exon 3), SEQ ID NO:9 (amino acids encoded by exon 4), SEQ ID NO:11 (amino acids encoded by exon 6) or SEQ ID NO:12 (amino acids encoded by exon 7). The amino acid sequence may be at least 80%, 81%, 82%, 83%, 84%, 85%, 86%, 87%, 88%, 89%, 90%, 91%, 92%, 93%, 94%, 95%, 96%, 97%, 98%, or 99% identical to the contiguous amino acids of 1) amino acids 24 to 47 of SEQ ID NO:15 and 2) each of SEQ ID NO:16 and SEQ ID NO:17. In particular embodiments, the variant RTEF-1 polypeptide does not include the N-terminal 23 amino acids of SEQ ID NO:15 (which corresponds to the N-terminal 23 amino acids of the amino acids encoded by exon 10). In particular embodiments, the polypeptide does not comprise the contiguous amino acids of SEQ ID NOs: 8, 9, 11, and 12.

In particular embodiments, the isolated variant RTEF-1 polypeptide is at least 80% identical to "RTEF-1 669" (SEQ ID NO:1) or "RTEF 366" (SEQ ID NO:2). In further embodiments, the RTEF-1 polypeptide is at least 82%, 84%, 86%, 88%, 90%, 91%, 92%, 93%, 94%, 95%, 96%, 97%, 98%, or 99% identical to SEQ ID NO:1 or SEQ ID NO:2. In a particular embodiment, the isolated variant RTEF-1 polypeptide comprises SEQ ID NO:1. In another particular embodiment, the isolated variant RTEF-1 polypeptide comprises SEQ ID NO:2. In even more specific embodiments, the RTEF-1 polypeptide consists essentially of SEQ ID NO:1 or SEQ ID NO:2. In further specific embodiments, the RTEF-1 polypeptide consists of SEQ ID NO:1 or SEQ ID NO:2.

In some embodiments, the variant RTEF-1 polypeptide is further defined as a dominant negative RTEF polypeptide (DN RTEF-1 polypeptide). This means that the RTEF-1 variant suppresses or reduces the activity of an intact RTEF-1 polypeptide. For example, in certain aspects, a DN RTEF-1 variant may be defined as a polypeptide that when expressed in a cell inhibits or reduces VEGF promoter activity. In particular embodiments, reduction in VEGF promoter activity is reduction relative to the VEGF promoter activity of a 1305 bp isoform having the sequence set forth in SEQ ID NO:6.

The variant RTEF-1 isoforms may or may not include the N-terminus of a human RTEF-1 polypeptide. In some embodiments, the RTEF-1 isoform includes the first 3, 4, 5, 6, 7, 8, 9, 10, 11, 12, 13, 14, 15, 20, 25, 30, 35, 40, 45, or 50 amino acids of the N-terminus of a human RTEF-1 polypeptide. In specific embodiments, the RTEF-1 isoform includes the first 9 amino acids of the N-terminus of RTEF-1. In a particular embodiment, the variant RTEF-1 isoform does not include an amino acid sequence consisting of amino acids 1-16 of SEQ ID NO:8.

Particular embodiments of the present variant RTEF-1 isoforms include the YAP binding domain. One particular variant, SEQ ID NO:1, includes the YAP binding domain. Another variant, SEQ ID NO:2, differs from RTEF-1 669 by lacking the first 5 β-sheets and two α-helices of the YAP binding domain (Chen et al., 2010; Li et al., 2010). Embodiments of the present variant RTEF-1 isoforms may harbor a range of YAP binding affinities which would be beneficial in modifying YAP activity, such as by suppressing YAP over activity.

In some embodiments of the present variant RTEF-1 polypeptides, the polypeptide does not include a nuclear localization signal. The variant RTEF-1 polypeptide can then be applied to suppress YAP activity in the cytoplasm of a target cell that may be overexpressing YAP, such as a cancer cell. In other embodiments, the variant RTEF-1 polypeptides include a nuclear translocation signal to target suppression of nuclear YAP activity within the nucleus of target cells, such as cancer cells that overexpress YAP. Nuclear localization signals are small (5-14) stretches of positively charged amino acids and are usually rich in arginine, lysine, histidine or glycine moieties. Non-limiting examples of nuclear localization signals include Pro-Pro-Lys-Lys-Lys-Arg-Lys-Val (SEQ ID NO:18) and Arg-Arg-Met-Lys-Trp-Lys-Lys (SEQ ID NO:19).

The variant RTEF-1 polypeptides set forth herein may optionally include a cell internalization moiety. The cell internalization moiety may be a polypeptide, an antibody, an aptamer or an avimer. Non-limiting examples of cell internalization moieties include a polypeptide from HIV tat, HSV-1 tegument protein VP22, or *Drosophila* antennopedia. Other examples include poly-arginine, poly-methionine or poly-glycine. In a specific embodiment, the cell internalization moiety includes RMRRMRRMRR (SEQ ID NO:20). In further embodiments, the cell internalization moiety is an antibody that is an IgA, an IgM, an IgE, an IgG, a Fab, a F(ab')2, a single chain antibody or a paratope peptide. The variant RTEF-1 polypeptides set forth herein may be obtained from natural sources or can be synthesized using any method known to those of ordinary skill in the art.

Thus, in certain cases, variant RTEF-1 fusion proteins are provided comprising a cell internalization moiety (and/or nuclear localization sequence) and a variant RTEF-1 polypeptide. The skilled artisan with understand that such fusion proteins may additionally comprises a one or more amino acid sequences operating the cell internalizing moiety and the variant RTEF-1 polypeptide sequence. For example, in some cases a linker sequence may separate these two domains. For example, a linker sequences may comprise a "flexible" amino acids with a large number or degrees of conformational freedom such as a poly glycine linker In some cases, a linker sequence may comprise a proteinase cleavage site. For instance, in certain aspects, a linker sequence may comprising a cleavage site that is recognized and cleaved by an intracellular proteinase thereby releasing a variant RTEF-1 sequence from the cell internalization sequence (or nuclear localization sequence) once the fusion protein has been internalized.

In further aspects of the invention a cell internalization moiety may be further defined as a cell-targeting moiety, which is a moiety that binds to or is internalized by only a selected population of cells such as cells expressing a particular cellular receptor. Such a cell targeting may, for example, comprise an antibody, a growth factor, a hormone, a cytokine, an aptamer or an avimer that binds to a cell surface protein. As used herein the term antibody may refer to an IgA, IgM, IgE, IgG, a Fab, a F(ab')2, single chain antibody or paratope peptide. In certain cases, a cell targeting moiety of the invention may target a particular type of cells such as a retinal, endothelial, iris or neuronal cell. In still further aspects a cell targeting moiety of the invention may be defined as cancer cell binding moiety. For example, in some very specific cases a cell targeting moiety of the invention may target a cancer cell associated antigen such a gp240 or Her-2/neu.

The variant RTEF-1 polypeptide may further include a cell secretion signal. The cell secretion signal may be any cell secretion signal known to those of ordinary skill in the art. For example, the cell secretion signal may include the human IL-2 secretion signal sequence (SEQ ID NO:23). In a particular aspect for example, a variant RTEF-1 polypeptide comprises a cellular secretion signal. Thus, in certain cases, a variant RTEF-1 polypeptide may comprise a cell internalization moiety and cell secretion signal, thereby allowing the polypeptide to be secreted by one cells and internalized into a surrounding a cell.

The present invention also includes nucleic acids that include a nucleic acid segment encoding any of the variant RTEF-1 polypeptides of the present invention. The nucleic acid may be a DNA or RNA. In some embodiments, the nucleic acid includes an expression cassette that includes an antiantiogenesis gene operably coupled to a promoter. As used herein the term "expression cassette" means that additional nucleic acids sequences are included that enable expression of a variant RTEF-1 in a cell, or more particularly in a eukaryotic cell. Such additional sequences may, for example, comprise a promoter, an enhancer, intron sequences (e.g., before after or with in the variant RTEF-1 coding region) or a polyadenylation signal sequence. The skilled artisan will recognize that sequences included in an expression cassette may be used to alter the expression characteristics of a variant RTEF-1 polypeptide. For instance, cell type specific, conditional or inducible promoter sequences may be used to restrict the variant RTEF-1 to selected cell types or growth conditions. Furthermore, it is contemplated that certain alterations may be made to the variant RTEF-1 polypeptide sequence in order to enhance expression from an expression cassette for example, as exemplified herein, the initiation codon of a variant RTEF-1 may be changes to ATG to facilitate efficient translation.

In still further embodiments, the present invention concerns methods for reducing or inhibiting RTEF-1 dependent transcriptional activity. As used herein the term RTEF-1 dependent transcriptional activity refers to transcription that is mediated or enhanced by expression of an full length or fully active RTEF-1 polypeptide, as exemplified by SEQ ID NO:1, or SEQ ID NO:2. Thus, in some respects, the invention provides methods for inhibiting or reducing VEGF promoter activity (and thereby VEGF expression) comprising expressing a DN RTEF-1 polypeptide in a cell. Thus, in a specific embodiment, there is provided a method for treating a patient with an angiogenic disorder comprising administering to the patient an effective amount of a therapeutic composition comprising a RTEF-1 dominant negative polypeptide or a nucleic acid expression vector encoding a RTEF-1 dominant negative polypeptide as described supra. In preferred aspects, methods described herein may used to treat a human patient.

The nucleic acid may optionally be included in a vector. The vector may be any vector known to those of ordinary skill in the art to target delivery of DNA to a particular cell. In particular embodiments, the vector is a viral vector or a liposome. Non-limiting examples of viral vectors include an adenovirus vector, an adeno-associated virus vector, a herpes virus vector, a SV40 virus vector, a retrovirus vector, or a vaccinia virus vector. In particular embodiments, the viral vector is a retrovirus vector. In a specific embodiment, the retrovirus vector is a lentiviral vector. Examples of lentiviral vectors contemplated as part of the invention include those vectors described in U.S. Pat. No. 7,122,181, herein specifically incorporated by reference. The lentiviral expression vector may optionally be an HIV vector. In some cases such lentiviral vectors may be self-inactivating (SIN) lentiviral vector such as those described in U.S. Applns. 20030008374 and 20030082789 incorporated herein by reference.

The promoter of the expression cassette may be any promoter known to those of ordinary skill in the art. For example, the promoter may be a cell type specific promoter or an inducible promoter. Non-limiting examples of inducible promoters include hypoxia inducible promoters and angiogenesis inducible promoters.

The antiangiogenesis gene included in the expression cassette may be any antiangiogenesis gene known to those of ordinary skill in the art. For example, in some aspects, the antiangiogenesis gene may be a tissue inhibitor of metalloproteinase, endostatin, angiostatin, endostatin XVIII, endostatin XV, kringle 1-5, PEX, the C-terminal hemopexin domain of matrix metalloproteinase-2, the kringle 5 domain of human plasminogen, a fusion protein of endostatin and angiostatin, a fusion protein of endostatin and the kringle 5 domain of human plasminogen, the monokine-induced by interferon-gamma (Mig), the interferon-alpha inducible protein 10 (IP10), a fusion protein of Mig and IP10, soluble FLT-1 (fms-like tyrosine kinase 1 receptor), and kinase insert domain receptor (KDR) gene. In certain specific aspects, such an angiogenic regulator gene may be delivered in a viral vector such as the lentiviral vectors described in U.S. Pat. No. 7,122,181, incorporated herein by reference. In particular embodiments, the expression cassette includes two or more antiangiogenesis genes. The two or more antiangiogenesis genes may be the same or may be distinct genes, such as any of the aforementioned genes.

The present invention also includes pharmaceutical compositions that include one or more variant RTEF-1 polypeptides of the present invention or one or more nucleic acids of the present invention, and a pharmaceutically acceptable carrier. Some of the compositions of the present invention may include at least one variant RTEF-1 polyp eptide and at least one nucleic acid encoding a variant RTEF-1 polypeptide. The pharmaceutical carrier may be any such carrier known to those of ordinary skill in the art. Non-limiting examples of carriers include water, saline, a dipolar aprotic solvent, an organic solvent, or a mixture thereof. The pharmaceutical compositions set forth herein may optionally include one or more additional excipients or therapeutic agents. In some embodiments, the pharmaceutical composition is included in a drug delivery device or coats a drug delivery device. The device may be a device designed to be applied to a surface of a subject or within a subject. In particular embodiments, the pharmaceutical composition comprises one or more variant RTEF-1 polypeptides that comprise SEQ ID NO:1 or SEQ ID NO:2.

Other aspects of the present invention concern methods of inducing cell contact inhibition in a population that includes two or more cells, comprising contacting a cell of the population with an effective amount of a variant RTEF-1 polypeptide of the present invention or a nucleic acid of the present invention, wherein cell contact inhibition in the population is induced.

Further embodiments of the invention concern methods of regulating size of an organ, that involve contacting an organ with an effective amount of a variant RTEF-1 polypeptide of the present invention or a nucleic acid of the present invention, wherein organ size is regulated. The variant RTEF-1 polypeptide or nucleic acid may be contacted with the organ in situ or in vivo.

Still further aspects of the invention concern methods of suppressing YAP activity in a cell that involve contacting a cell with an effective amount of a variant RTEF-1 polypeptide of the present invention or a nucleic acid of the present invention, wherein YAP activity in the cell is suppressed. The cell may be a cell that demonstrates detectable levels of YAP in the nucleus and/or the cytoplasm of the cell. The cell may be a cell that overexpresses YAP in the nucleus or cytoplasm. Non-limiting examples of such cells include cancer cells, such as colon adenocarcinoma cells, lung adenocarcinoma cells, and ovarian serous cystadenocarinoma cells. It has been noted that loss of either critical components of the Hippo pathway or overexpression of YAP can lead to uncontrolled growth and survival. Thus, reduction of YAP activity can be a strategy for reducing uncontrolled growth and prolonging survival in subjects with tumors that overexpress YAP. To target suppression of YAP in the nucleus of a cell, the variant RTEF-1 polypeptide may be engineered to include a nuclear localization sequence. To target reduction of YAP in the cytoplasm of a cell, the variant RTEF-1 polypeptide may be engineered to not include a nuclear localization sequence. Upon RTEF-1 binding, YAP would be unable to associate with 14-3-3 proteins.

Further embodiments of the present invention concern methods of treating a subject with a disorder that involves administering to the subject an effective amount of a pharmaceutical composition comprising one or more variant RTEF-1 polypeptides of the present invention or one or more nucleic acids encoding a variant RTEF-1 polypeptide of the present invention, wherein the subject is treated. In some embodiments, the subject has a disorder associated with abnormal cell growth or abnormal cell proliferation or reduced apoptosis. The disease may be an angiogenic disorder. Non-limiting examples of angiogenic disorders include cancer, ocular neovascularization, an arterio-venous malformation, coronary restenosis, peripheral vessel restenosis, glomerulonephritis, or rheumatoid arthritis. Thus, in certain cases, methods of the invention may be used to treat ocular disorders such as macular degeneration (e.g., age-related macular degeneration (AMD)), corneal graft rejection, corneal neovascularization, retinopathy of prematurity (ROP) and diabetic retinopathy (DR). For example, methods of the invention may be used in the treatment of wet or dry AMD. Thus, in certain cases, methods of the invention may be used to treat a number AMD associated ocular lesions such as predominantly classic, minimally classic, and occult with no classic lesions (Gragoudas et al., 2004).

In a particular embodiment, the disorder is cancer. Non-limiting examples of cancer include cancer of breast cancer, lung cancer, prostate cancer, leukemia, lymphoma, head and neck cancer, brain cancer, stomach cancer, intestinal cancer, colorectal cancer, renal cancer, bladder cancer, testicular cancer, esophageal cancer, ocular melanoma, retinoblastoma, liver cancer, ovarian cancer, skin cancer, cancer of the tongue, cancer of the mouth, or metastatic cancer. In some embodiments, the cancer cells demonstrate detectable YAP in the nucleus and/or cytoplasm. In more particular embodiments, the cancer cells demonstrate detectable YAP in the nucleus and the cytoplasm. In further embodiments, the cancer cells demonstrate overexpression of YAP in the nucleus and/or cytoplasm compared to expression of YAP in the nucleus and/or cytoplasm of a cell of a similar tissue type that is not cancerous. For example, the cancer may be a breast cancer cell from a subject, and the cell of a similar tissue type would be a breast tissue cell of the subject that is not cancerous. Furthermore additional anticancer therapies may be used in combination or in conjunction with methods of the invention. Such additional therapies may be administered before, after or concomitantly with methods of the invention. For example an additional anticancer therapy may be a chemotherapy, surgical therapy, an immunotherapy and/or radiation therapy.

In certain particular embodiments, the angiogenic disorder is ocular neovascularization. Non-limiting examples of ocular neovascularization include neovascularization due to age-related macular degeneration, neovascularization due to corneal graft rejection, neovascularization due to retinopathy of prematurity (ROP), or neovascularization due to diabetic retinopathy.

The methods of the present invention may further involve administering to the subject one or more secondary therapies for treatment of a disorder. For example, the secondary therapy may be a secondary therapy of an angiogenic disorder, a disorder associated with abnormal cell growth, a disorder associated with abnormal organ growth, or a disorder associated with impaired cell contact inhibition, or a disorder associated with increased YAP activity.

In some embodiments, the secondary therapy is an antibody that binds to VEGF, a VEGF receptor, FGF, an FGF receptor, bevacizumab, ranibizumab, or pegaptanib sodium. The secondary therapy may be an anticancer therapy that is chemotherapy, surgical therapy, immunotherapy or radiation therapy. In particular embodiments, the subject is a mammal. Non-limiting examples of mammals include mice, rats, rabbits, dogs, cats, goats, sheep, horses, cows, primates, and humans. In specific embodiments, the subjects are humans.

Administration of the compositions set forth herein may be by any method known to those of ordinary skill in the art. Non-limiting examples of routes of administration include intravenously, intraarterially, epidurally, intrathecally, intraperitoneally, subcutaneously, orally, or topically. In some embodiments directed at the treatment or prevention of an ocular disorder, the composition is administered locally to the eye by topical drops, intracameral injection, subconjunctival injection, subtenon injection, or by intravitreous injection. Further detail concerning administration and dosage is discussed in the specification below.

Further aspects of the present invention concern kits that include a predetermined quantity of one or more variant RTEF-1 polypeptides of the present invention or one or more nucleic acids of the present invention in one or more sealed vials. The kits may include one or more components, such as vials, syringes, tubes, and instructions for use.

In some further embodiments there is provided a pharmaceutical composition of the invention comprised in a bottle where the bottle includes an exit portal that enables drop-wise administration of the composition. In some cases, a pharmaceutical composition comprised in a bottle comprises multiple doses however in certain aspects a bottle comprises a single dose unit for administration to one or two eyes, preferable a single dose unit is comprised in 1-2 drops of the formulation. As used herein the term "bottle" refers to any fluid container such as an ampoule, dropper or syringe.

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

FIG. 1A, 1B, 1C, 1D. Bar diagrams demonstrating relative VEGF promoter activity per different variant RTEF-1 isoforms. Bars for hypoxia are on the right, and bars for normoxia are on the left. 1A—HEK 293 (p7), hypoxia vs. normoxia; 1B—Hek 293 (p7), hypoxia vs. normoxia omitting 447; 1C—VEGF promoter activity fold change; 1D—VEGF promoter activity fold change, omitting 447 from the table.

FIG. 2A, 2B, 2C. Schematic of RTEF-1 isoforms. 2A—summary schematic of isoforms; 2B—1305 pb, 963 bp, 651 bp, and 447 bp isoforms; 2C—669 bp and 366 bp isoforms. The gray and black diagonally striped bar indicates the TEA DNA binding domain. The black and white diagonal stripes within the Tea Domain represent 3 helices. The grey square shows the position of a putative nuclear localization signal. The vertical striped bar indicates the position of the proline rich domain (PRD). The horizontal striped bars indicate the position of the 2 separate STY domains.

FIG. 3. Schematic showing DNA binding domain and YAP binding domain for RTEF-1 isoforms. The underlined section is the TEA DNA binding domain, and the gray shaded section is the YAP binding domain (SEQ ID NO:3).

FIG. 4. RT-PCR for potential RTEF-1 interacting cofactor proteins within human RVEC, RPE (ARPE-19) and 293T cells.

DETAILED DESCRIPTION OF THE INVENTION

Figure 1D:
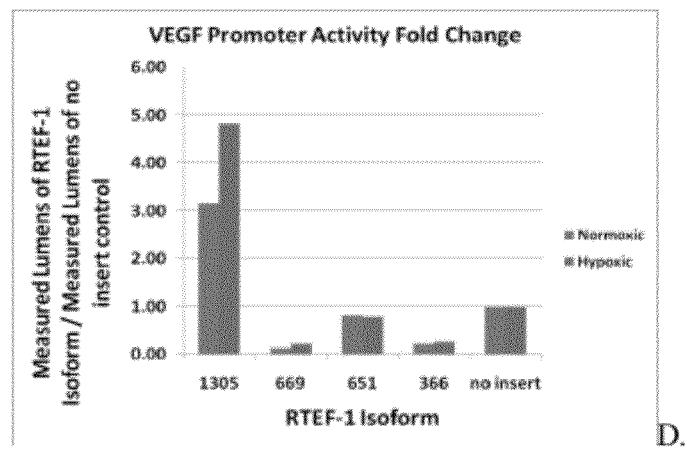

Recently a number of strategies have been developed to inhibit angiogenic signaling. In particular, a number of strategies have focused on blockade of VEGF signaling by inhibiting the binding of VEGF with one or both of its cell surface receptors. However, these strategies are unable to address the initial production of VEGF that initiates aberrant angiogenesis. Thus, new methods and compositions that inhibit VEGF production may provide new methods for VEGF blockade and treatments for resultant angiogenesis. To this end, in certain aspects, the instant invention provides variant RTEF-1 polypeptides that inhibit VEGF signaling. Furthermore, since the instant invention concerns the targeting of intracellular processes, therapeutics of the invention may be targeted to specific cell types thereby reducing undesirable systemic side effects. Thus, the instant inventions offers new methods to treat angiogenic disorders and/or ways to enhance the effectiveness of current VEGF blockade strategies.

RTEF-1 a member of a family of multifunctional transcription factors and has been shown to be an activator of VEGF transcription, including hypoxia induced VEGF transcription. The instant invention provides the basis for new variant RTEF-1 polypeptides and the use thereof to prevent or inhibit angiogenic disorders. DN RTEF-1 polypeptides may be delivered directly to the intra cellular milieu or expressed in targeted cells to blockade VEGF production. Such dominate negative polypeptides down regulate not only nascent VEGF production but also production of VEGF that is normally stimulated by RTEF-1 such as during hypoxia. Thus, compositions of the invention, may be used to reduce the ability of targeted cells and tissues to recruit new blood vessel formation. This is of great interest in, for example, in disorders such as cancer and ocular neovascular disorders where the production of new blood vessels is directly related to the pathogenesis of the disease. Furthermore, the variant RTEF-1 polypeptides may be used to treat tumors or tumor metastases by reducing their ability to gain nutrients through new blood vessel formation. Thus, methods to slow tumor growth and/or induce tumor regression are also provided. Furthermore, since compositions of the invention target intracellular transcription, compositions of the invention may be used to target effected tissues by used of specific cell targeting/internalization moieties and thereby reducing the side effects in other non-targeted tissues.

I. Variant RTEF-1 Polypeptides

A number of variant RTEF-1 polypeptides are described and functionally characterized herein. For example, particular examples as set forth as follows:

SEQ ID NO: 1, encoded by a 669 bp RTEF-1 human cDNA that is 222 amino acid protein, as the following sequence:

MEGTAGTITSKLWMLEFSAFLEQQQDPDTYNKHLFVHIGQSSPSYSDPYLEAVDIRQIYD

KFPEKKGGLKDLFERGPSNAFFLVKFWADLNTNIEDEGSSFYGVSSQYESPENMIITCST

KVCSFGKQVVEKVETEYARYENGHYSYRIHRSPLCEYMINFIHKLKHLPEKYMMNSVL

ENFTILQVVTNRDTQETLLCIAYVFEVSASEHGAQHHIYRLVKE

SEQ ID NO: 2, encoded a 366 bp human cDNA is a 121 amino acid protein having the sequence:

MEGTAGTITPENMIITCSTKVCSFGKQVVEKVETEYARYENGHYSYRIHRSPLCEYMINF

IHKLKHLPEKYMMNSVLENFTILQVVTNRDTQETLLCIAYVFEVSASEHGAQHHIYRLV

KE

SEQ ID NO: 3, encoded by a 1305 bp human cDNA is a 434 amino acid protein having the sequence:

MEGTAGTITSNEWSSPTSPEGSTASGGSQALDKPIDNDAEGVWSPDIEQSFQEALAIYPPC

GRRKIILSDEGKMYGRNELIARYIKLRTGKTRTRKQVSSHIQVLARRKAREIQAKLKDQA

AKDKALQSMAAMSSAQIISATAFHSSMALARGPGRPAVSGFWQGALPGQAGTSHDVKP

FSQQTYAVQPPLPLPGFESPAGPAPSPSAPPAPPWQGRSVASSKLWMLEFSAFLEQQQDP

DTYNKHLFVHIGQSSPSYSDPYLEAVDIRQIYDKFPEKKGGLKDLFERGPSNAFFLVKFW

ADLNTNIEDEGSSFYGVSSQYESPENMIITCSTKVCSFGKQVVEKVETEYARYENGHYSY

RIHRSPLCEYMINFIHKLKHLPEKYMMNSVLENFTILQVVTNRDTQETLLCIAYVFEVSA

SEHGAQHHIYRLVKE

SEQ ID NO: 4, encoded by a 936 bp human cDNA is a 311 amino acid protein having the sequence:

MEGTAGTITSNEWSSPTSPEGSTASGGSQALDKPIDNDAEGVWSPDIEQSFQEALAIYPPC

GRRKIILSDEGKMYGRNELIARYIKLRTGKTRTRKQVSSHIQVLARRKAREIQAKLKYNK

HLFVHIGQSSPSYSDPYLEAVDIRQIYDKFPEKKGGLKDLFERGPSNAFFLVKFWADLNT

NIEDEGSSFYGVSSQYESPENMIITCSTKVCSFGKQVVEKVETEYARYENGHYSYRIHRS

PLCEYMINFIHKLKHLPEKYMMNSVLENFTILQVVTNRDTQETLLCIAYVFEVSASEHGA

QHHIYRLVKE

SEQ ID NO: 5, encoded by a 651 bp human cDNA is a 216 amino acid protein having the sequence:

MEGTAGTITSNEWSSPTSPEGSTASGGSQALDKPIDNDAEGVWSPDIEQSFQEALAIYPPC

GRRKIILSDEGKMYGRNELIARYIKLRTGKTSSFYGVSSQYESPENMIITCSTKVCSFGKQ

VVEKVETEYARYENGHYSYRIHRSPLCEYMINFIHKLKHLPEKYMMNSVLENFTILQVV

TNRDTQETLLCIAYVFEVSASEHGAQHHIYRLVKE

SEQ ID NO: 6, encoded by a 447 bp human cDNA is a 148 amino acid protein having the sequence:

MEGTAGTITSNEWSSPTSPEGSTASGGSQALDKPIDNDGEGVWSPDIEQSFQEALAIYPPC

GRRKIILSDEGKMYGRNELIARYIKLRTGKTRTRKQVSSHIQVLARRKAREIQAKLKFWQ

GALPGQAETSHDVKPFSQHHIYRLVKE

As described supra, in certain aspects of the invention a dominant negative (DN) RTEF-1 polypeptide may comprise one or more internal amino acid deletions.

TABLE 1

RTEF-1 amino acid sequence by encoding exon

Exon Amino acid sequence encoded

1  N/A

2  LEGTAGTITSNEWSSPTSPEGSTASGGSQALDKPIDNDAEGVWSPDIEQSFQEALAIY
   PPCGRRKIILSDEGKMYG* (SEQ ID NO: 7)

3  RNELIARYIKLRTGKTRTRKQ (SEQ ID NO: 8)

4  VSSHIQVLARRKAREIQAKLK (SEQ ID NO: 9)

5  DQAAKDKALQSMAAMSSAQIISATAFHSSMALARGPGRPAVSG (SEQ ID NO: 10)

6  FWQGALPGQAGTSHD* (SEQ ID NO: 11)

7  VKPFSQQTYAVQPPLPLPG* (SEQ ID NO: 12)

8  FESPAGPAPSPSAPPAPPWQGRSVASSKLWMLEFSAFLEQQQDPDT (SEQ ID NO: 13)

9  YNKHLFVHIGQSSPSYSDPYLEAVDIRQIYDKFPEKKGGLKDLFERGPSNAFFLVKFW
   (SEQ ID NO: 14)

10 ADLNTNIEDEGSSFYGVSSQYESPENMIITCSTKVCSFGKQVVEKVE (SEQ ID NO: 15)

11 TEYARYENGHYSYRIHRSPLCEYMINFIHKLKHLPEKYMMNSVLENFTILQ (SEQ ID NO: 16)

12 VVTNRDTQETLLCIAYVFEVSASEHGAQHHIYRLVKE (SEQ ID NO: 17)

*Indicates amino acids that are encoded by nucleic acid codons that are split between exons.

In additional aspects of the invention, variant RTEF polypeptides may be further modified by one or more amino substitutions while maintaining their transcriptional functions. For example, amino acid substitutions can be made at one or more positions wherein the substitution is for an amino acid having a similar hydrophilicity. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in an RETF-1 sequence and will likely only have minor effects on their activity and ability to repress VEGF promoter activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the DN RTEF-1 polypeptides described herein may be modified by the substitution of an amino acid, for different, but homologous amino acid with a similar hydrophilicity value. Amino acids with hydrophilicities within +/−1.0, or +/−0.5 points are considered homologous.

Additional information concerning variant RTEF-1 polypeptides can be found in U.S. Patent App. Publ. No. 2009-0117119, herein specifically incorporated by reference in its entirety.

II. Cell Internalization and Targeting Moieties

Cell internalization moieties for use herein may be any molecule in complex (covalently or non-covalently) with a variant RTEF-1 that mediate transport of the variant RTEF-1 across a cell membrane. Such internalization moieties may be peptides, polypeptides, hormones, growth factors, cytokines, aptamers or avimers. Furthermore, cell internalization moiety may mediate non-specific cell internalization or be a cell targeting moiety that is internalized in a subpopulation of targeted cells.

For example, in certain embodiments, cell targeting moieties for use in the current invention are antibodies. In general the term antibody includes, but is not limited to, polyclonal antibodies, monoclonal antibodies, single chain antibodies, humanized antibodies, minibodies, dibodies, tribodies as well as antibody fragments, such as Fab', Fab, F(ab')2, single domain antibodies and any mixture thereof. In some cases it is preferred that the cell targeting moiety is a single chain antibody (scFv). In a related embodiment, the cell targeting domain may be an avimer polypeptide. Therefore, in certain cases the cell targeting constructs of the invention are fusion proteins comprising a variant RTEF-1 and a scFv or an avimer. In some very specific embodiments the cell targeting construct is a fusion protein comprising variant RTEF-1 polypeptide fused to a single chain antibody.

In certain aspects of the invention, a cell targeting moieties may be a growth factor. For example, transforming growth factor, epidermal growth factor, insulin-like growth factor, fibroblast growth factor, B lymphocyte stimulator (BLyS), heregulin, platelet-derived growth factor, vascular endothelial growth factor (VEGF), or hypoxia inducible factor may be used as a cell targeting moiety according to the invention. These growth factors enable the targeting of constructs to cells that express the cognate growth factor receptors. For example, VEGF can be used to target cells that express FLK-1 and/or Flt-1. In still further aspects the cell targeting moiety may be a polypeptide BLyS (see U.S. Appln. 20060171919).

In further aspects of the invention, a cell targeting moiety may be a hormone. Some examples of hormones for use in the invention include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36. As discussed above targeting constructs that comprise a hormone enable method of targeting cell populations that comprise extracelluar receptors for the indicated hormone.

In yet further embodiments of the invention, cell targeting moieties may be cytokines For example, IL1, IL2, IL3, IL4, IL5, IL6, IL7, IL8, IL9, IL10, IL11, IL12, IL13, IL14, IL15, IL-16, IL-17, IL-18, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1α, IL-1β, IL-1 RA, MIF and IGIF may all be used as targeting moieties according to the invention.

In certain aspects of the invention a cell targeting moiety of the invention may be a cancer cell targeting moiety. It is well known that certain types of cancer cells aberrantly express surface molecules that are unique as compared to surrounding tissue. Thus, cell targeting moieties that bind to these surface molecules enable the targeted delivery of variant RTEF-1 specifically to the cancers cells. For example, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cancer cell. The skilled artisan will understand that the effectiveness of cancer cell targeted variant RTEF-1 may, in some cases, be contingent upon the expression or expression level of a particular cancer marker on the cancer cell. Thus, in certain aspects there is provided a method for treating a cancer with targeted variant RTEF-1 comprising determining whether (or to what extent) the cancer cell expresses a particular cell surface marker and administering variant RTEF-1 targeted therapy (or another anticancer therapy) to the cancer cells depending on the expression level of a marker gene or polypeptide.

As discussed above cell targeting moieties according to the invention may be, for example, an antibody. For instance, a cell targeting moiety according the invention may bind to a skin cancer cell such as a melanoma cell. It has been demonstrated that the gp240 antigen is expressed in variety of melanomas but not in normal tissues. Thus, in certain aspects of the invention, there is provided a cell targeting construct comprising an variant RTEF-1 and a cell targeting moiety that binds to gp240. In some instances, the gp240 binding molecule may be an antibody, such as the ZME-018 (225.28S) antibody or the 9.2.27 antibody. In an even more preferred embodiment, the gp240 binding molecule may be a single chain antibody such as the scFvMEL antibody.

In yet further specific embodiments of the invention, cell targeting constructs may be directed to breast cancer cells. For example cell targeting moieties that bind to Her-2/neu, such as anti-Her-2/neu antibodies may conjugated to a variant RTEF-1. One example of a such cell targeting constructs are fusion proteins comprising the single chain anti-Her-2/neu antibody scFv23 and variant RTEF-1. Other scFv antibodies such as scFv(FRP5) that bind to Her-2/neu may also be used in the compositions and methods of the current invention (von Minckwitz et al., 2005).

In certain additional embodiments of the invention, it is envisioned that cancer cell targeting moieties according to invention may have the ability to bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example are the cell targeting agents described in U.S. Appln. 2004005647 and in Winthrop et al., 2003 that bind to MUC-1 an antigen that is expressed on a variety cancer types. Thus, it will be understood that in certain embodiments, cell targeting constructs according the invention may be targeted against a plurality of cancer or tumor types.

III. Methods for Producing Antibodies

The following methods exemplify some of the most common antibody production methods.

A. Polyclonal Antibodies

Polyclonal antibodies generally are raised in animals by multiple subcutaneous (sc) or intraperitoneal (ip) injections of the antigen. As used herein the term "antigen" refers to any polypeptide that will be used in the production of a antibodies. Antigens for use according to the instant invention include in certain instances, cancer cell surface marker polypeptides and eye specific cell surface markers.

It may be useful to conjugate an antigen or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1 N=C=NR$, where R and $R^1$ are different alkyl groups.

Animals are immunized against the immunogenic conjugates or derivatives by combining 1 mg of 1 μg of conjugate (for rabbits or mice, respectively) with 3 volumes of Freud's complete adjuvant and injecting the solution intradermally at multiple sites. One month later the animals are boosted with ⅕ to ¹⁄₁₀ the original amount of conjugate in Freud's complete adjuvant by subcutaneous injection at multiple sites. 7 to 14 days later the animals are bled and the serum is assayed for specific antibody titer. Animals are boosted until the titer plateaus. Preferably, the animal boosted with the same antigen conjugate, but conjugated to a different protein and/or through a different cross-linking reagent. Conjugates also can be made in recombinant cell culture as protein fusions. Also, aggregating agents such as alum are used to enhance the immune response.

B. Monoclonal Antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, monoclonal antibodies of the invention may be made using the hybridoma method first described by Kohler & Milstein (1975), or may be made by recombinant DNA methods (U.S. Pat. No. 4,816,567).

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding 1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Culture medium in which hybridoma cells are growing is assayed for production of monoclonal antibodies directed against the target antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard (1980).

After hybridoma cells are identified that produce antibodies of the desired specificity, affinity, and/or activity, the clones may be subcloned by limiting dilution procedures and grown by standard methods, Goding (1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al. (1984), or by covalently joining to the immunoglobulin coding sequence all or part of the coding sequence for a non-immunoglobulin polypeptide. In that manner, "chimeric" or "hybrid" antibodies are prepared that have the binding specificity for any particular antigen described herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for the target antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; biotin; radioactive isotopic labels, such as, e.g., $^3$H, $^{14}$C, $^{32}$P, $^{35}$S, or $^{125}$I, or an enzyme, such as alkaline phosphatase, beta-galactosidase or horseradish peroxidase.

Any method known in the art for separately conjugating the antibody to the detectable moiety may be employed, including those methods described by Hunter et al. (1962); David et al. (1974); Pain et al. (1981); and Nygren (1982).

The antibodies of the present invention may be employed in any known assay method, such as competitive binding assays, direct and indirect sandwich assays, and immunoprecipitation assays (Zola, 1987).

Competitive binding assays rely on the ability of a labeled standard (which may be a purified target antigen or an immunologically reactive portion thereof) to compete with the test sample analyte for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

C. Humanized Antibodies

As discussed previously, antibodies for use in the methods of the invention may be polyclonal or monoclonal antibodies or fragments thereof. However, in some aspects it is preferred that the antibodies are humanized such that they do not illict an immune response in subject being treated. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., 1986); Riechmann et al., 1988; Verhoeyen et al., 1988), by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties, for example the ability bind to and are internalized by a target cell. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

D. Human Antibodies

Human monoclonal antibodies can be made by the hybridoma method. Human myeloma and mouse-human heteromyeloma cell lines for the production of human monoclonal antibodies have been described, for example, by Kozbor (1984) and Brodeur et al. (1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al. (1993); Jakobovits et al. (1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g. Johnson et al. (1993). Several sources of V-gene segments can be used for phage display. Clackson et al. (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al. (1991), or Griffith et al. (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al. (1993), and the isolation of a high affinity human antibody directly from such large phage library has been reported. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

IV. Nucleic Acid Molecules

In certain aspects, the instant invention concerns nucleic acid molecules encoding a variant RTEF-1 polypeptide as set forth herein. In certain aspects, a nucleic acid sequence is comprised in a nucleic acid vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et. al., 1998), murine epididymal retinoic acid-binding gene (Lareyre et. al., 1999), human CD4 (Zhao-Emonet et. al., 1998), mouse alpha2 (XI) collagen (Tsumaki, et. al., 1998), DIA dopamine receptor gene (Lee, et. al., 1997), insulin-like growth factor II (Wu et. al., 1997), and human platelet endothelial cell adhesion molecule-1 (Almendro et. al., 1996).

B. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements, such as a Kozak sequence, which is comprised of the following sequence and spans the initiation codon AUG (ACCaugG).

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES element from a mammalian message (Macejak and Sarnow, 1991). IRES elements can be linked to heterologous open reading frames. Multiple open reading frames can be transcribed together, each separated by an IRES element, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

C. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et. al., 1999, Levenson et. al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et. al., 1997, herein incorporated by reference.)

E. Termination Signals

The vectors or constructs of the present invention will generally comprise at least one termination signal. A "termination signal" or "terminator" is comprised of the DNA sequences involved in specific termination of an RNA transcript by an RNA polymerase and these include; UGA, UAA and UAG. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site (AAUAAA). This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences. In certain specific cases a polyadenylation signal may be the signal from neuropilin-1 as described in U.S. Appln. 20050175591.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

F. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

G. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

H. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTM 11 may be utilized in making a recombinant phage vector which can be used to transform host cells, such as, for example, E. coli LE392.

Further useful plasmid vectors include pIN vectors (Inouye et. al., 1985); and pGEX vectors, for use in generating glutathione S transferase (GST) soluble fusion proteins for later purification and separation or cleavage. Other suitable fusion proteins are those with β galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

I. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). DN RTEF-1 components of the present invention may be a viral vector that encodes a DN RTEF-1 pollypeptide. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et. al., 1992; Curiel, 1994). Adeno associated virus (AAV) is an attractive vector system for use in the delivery of DN RTEF-1 expression cassettes of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et. al., 1984; Laughlin et. al., 1986; Lebkowski et. al., 1988; McLaughlin et. al., 1988). Details concerning the generation and use of rAAV vectors are described in U.S. Pat. Nos. 5,139,941 and 4,797,368, each incorporated herein by reference.

3. Retroviral Vectors

Retroviruses have promise as DN RTEF-1 delivery vectors in therapeutics due to their ability to integrate their genes into the host genome, transferring a large amount of foreign genetic material, infecting a broad spectrum of species and cell types and of being packaged in special cell lines (Miller, 1992).

In order to construct a DN RTEF-1 retroviral vector, a nucleic acid (e.g., one encoding a DN RTEF-1) is inserted into the viral genome in the place of certain viral sequences to produce a virus that is replication defective. In order to produce virions, a packaging cell line containing the gag, pol, and env genes but without the LTR and packaging components is constructed (Mann et. al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et. al., 1983). The media containing the recombinant retroviruses is then collected, optionally concentrated, and used for gene transfer. Retroviral vectors are able to infect a broad variety of cell types. However, integration and stable expression require the division of host cells (Paskind et. al., 1975).

Lentiviruses are complex retroviruses, which, in addition to the common retroviral genes gag, pol, and env, contain other genes with regulatory or structural function. Methods for delivery of antiangiogenic molecules with lentiviral vectors have been previously described, see for example U.S. Pat. No. 7,122,181, U.S. Patent App. Publ. Nos. 20090148936, 20060062765, 20030082159, and 20020114783, each of which is incorporated herein by reference in its entirety. Lentiviral vectors are well known in the art (see, for example, Naldini et. al., 1996; Zufferey et. al., 1997; Blomer et. al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et. al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et. al., 1988; Horwich et. al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et. al., 1989). Using antibodies against major histocompatibility complex class I and class II antigens, they demonstrated the infection of a variety of human cells that bore those surface antigens with an ecotropic virus in vitro (Roux et. al., 1989).

J. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et. al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et. al., 1986; Potter et. al., 1984); by calcium phosphate precipitation (Graham and Van Der Eb, 1973; Chen and Okayama, 1987; Rippe et. al., 1990); by using DEAE dextran followed by polyethylene glycol (Gopal, 1985); by direct sonic loading (Fechheimer et. al., 1987); by liposome mediated transfection (Nicolau and Sene, 1982; Fraley et. al., 1979; Nicolau et. al., 1987; Wong et. al., 1980; Kaneda et. al., 1989; Kato et. al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et. al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et. al., 1993; U.S. Pat. Nos. 4,684,611 and 4,952,500, each incorporated herein by reference); by desiccation/inhibition mediated DNA uptake (Potrykus et. al., 1985), and any combination of such methods. Through the application of techniques such as these, organelle(s), cell(s), tissue(s) or organism(s) may be stably or transiently transformed.

V. Therapeutic Methods

A. Pharmaceutical Preparations

Therapeutic compositions for use in methods of the invention may be formulated into a pharmacologically acceptable format. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one variant RTEF-1 polypeptide or nucleic acid active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments, the compositions of the present invention are suitable for application to mammalian eyes. For example, the formulation may be a solution, a suspension, or a gel. In some embodiments, the composition is administered via a bioerodible implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

Furthermore, the therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired. Thus, in some case dosages can be determined by measuring for example changes in serum insulin or glucose levels of a subject.

Precise amounts of the therapeutic composition may also depend on the judgment of the practitioner and are peculiar to each individual. Factors affecting the dose include the physical and clinical state of the patient, the route of administration, the intended goal of treatment (e.g., alleviation of symptoms versus attaining a particular serum insulin or glucose concentration) and the potency, stability and toxicity of the particular therapeutic substance.

In particular embodiments, the compositions of the present invention are suitable for application to mammalian eyes. For example, the formulation may be a solution, a suspension, or a gel. In some embodiments, the composition is administered via a bioerodible implant, such as an intravitreal implant or an ocular insert, such as an ocular insert designed for placement against a conjunctival surface. In some embodiments, the therapeutic agent coats a medical device or implantable device.

In preferred aspects the formulation of the invention will be applied to the eye in aqueous solution in the form of drops. These drops may be delivered from a single dose ampoule which may preferably be sterile and thus rendering bacteriostatic components of the formulation unnecessary. Alternatively, the drops may be delivered from a multi-dose bottle which may preferably comprise a device which extracts preservative from the formulation as it is delivered, such devices being known in the art.

In other aspects, components of the invention may be delivered to the eye as a concentrated gel or similar vehicle which forms dissolvable inserts that are placed beneath the eyelids.

B. Additional Therapies

As discussed supra in certain aspects therapeutic methods of the invention may be used in combination or in conjunction with additional antiangiogenic or anticancer therapies.

1. Chemotherapy

In certain embodiments of the invention DN RTEF-1 is administered in conjunction with a chemo therapeutic agent. For example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, gemcitabien, navelbine, farnesyl-protein tansferase inhibitors, trans-platinum, 5-fluorouracil, vincristin, Velcade, vinblastin and methotrexate, or any analog or derivative variant of the foregoing may used in methods according to the invention.

2. Radiotherapy

In certain further embodiments of the invention, compositions of the invention may be used to sensitize cell to radiation therapy. Radio therapy may include, for example, γ-rays, X-rays, and/or the directed delivery of radioisotopes to tumor cells. In certain instances microwaves and/or UV-irradiation may also used according to methods of the invention. Dosage ranges for X-rays range from daily doses of 50 to 200 roentgens for prolonged periods of time (3 to 4 wk), to single doses of 2000 to 6510 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radio therapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B, Her-2/neu, gp240 and p155.

4. Genes

In yet another embodiment, gene therapy in which a therapeutic polynucleotide is administered before, after, or at the same time as a cell targeting construct of the present invention. Delivery of variant RTEF-1 in conjunction with a vector encoding one or more additional gene products may have a combined anti-hyperproliferative effect on target tissues. A variety of genes are encompassed within the invention, for example a gene encoding p53 may be delivered in conjunction with variant RTEF-1 compositions.

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. A variant RTEF-1 therapy of the invention may be employed alone or in combination with a cytotoxic therapy as neoadjuvant surgical therapy, such as to reduce tumor size prior to resection, or it may be employed as postadjuvant surgical therapy, such as to sterilize a surgical bed following removal of part or all of a tumor.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Agents

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Relative VEGF Promoter Activity of Variant RTEF-1 Isoforms

Studies were conducted to examine the relative VEGF promoter activity of selected isoforms of RTEF.

The pSEAP assay is essentially a chemiluminescence assay in which two plasmids are electroporated into cells. One plasmid (pcDNA) contains a specific RTEF-1 isoform and the other plasmid (pSEAP plasmid) contains the VEGF promoter fused to the secreted alkaline phosphatase gene. Transcriptional activity on the exogenous VEGF promoter results in a secretable, thermo-stable, alkaline phosphatase (AP) protein. The abundance of AP protein can be measured by a luminescene assay. Thus, the measured lumens are indicative of the amount of AP in the media, which is a directly correlated to the activity on the promoter (human VEGF) driving the expression of the AP gene. Lumens measured from the 'no insert' control are indicative of the endogenous transcription factors (and cofactors) acting upon the exogenous VEGF promoter.

Cells were grown to approximately 80% confluency. Cells were trypsinized, washed with 8 mls of serum containing media and centrifuged at 1000 rpm for 5 minutes. The media was removed and cells were resuspended in an appropriate volume of solution V transfection reagent (AMAXA). One hundred microliters of the cell mix was added to electroporation cuvettes (AMAXA) containing 2 μg of a pcDNA RTEF-1 isoform expression vector along with 2 μg of the pSEAP expression vector under the control of the human VEGF promoter either containing or lacking the HRE element. Cells were transfected with the electroporation apparatus (AMAXA) using a predetermined optimized transfection program. Cells were then plated into either 6-well or 24-well plates and incubated overnight in 3 mls or 1 ml of appropriate media respectively. The following day the media was changed to 2% serum using a minimal volume to completely cover the cells. Cells were divided into either an atmospheric oxygen environment (normoxic) or a 1% oxygen environment (hypoxic). Cells were incubated in these states for 24-48 hours. Following the time course, cell media was collected and used to perform a secretable alkaline phosphate assay following manufactures protocols (Clontech). Briefly, 25 μl of media was added to 75 μl of dilution buffer, plated into 96 well plate and incubated at 65° C. for 30 minutes. The plate was then cooled on ice for 3 minutes and allowed to equilibrate to room temperature. 100 μl of pSEAP substrate solution was added to each well and incubated away from light for 15-30 minutes. Plates were then read within 60 minutes using plate reader capable of detecting luminescence.

RTEF-1 isoforms effect the VEGF promoter differently. Cells are cotransfected (Amaxa Nucleofector machine program AO23), plated, and allowed to recover in 10% serum media overnight at 37° C. and 5% $CO_2$. The media is changed to that of 2% serum the next morning. One of the duplicate trays are placed in a hypoxic chamber and flushed for 8 min. at 20 liters/min with 1% $O_2$, 5% $CO_2$, and 94% $N_2$. The hypoxic chamber is then sealed. Both the hypoxic chamber and the 'normoxic' tray are placed into the incubator (37° C. with 5% $CO_2$). The hypoxic chamber is flushed as previously done after 7 hrs and both trays are placed into the incubator overnight. The next morning, the hypoxic chamber is flushed once more as noted above and place into the incubator. Media is collected 2-3 hours later. Time in hypoxic chamber is ~27-48 hrs.

Results are shown in FIG. 1A-1D. The fold changes for each isoform are listed in Table 2. RTEF-1 isoform 1305 and 447 stimulate activity of the VEGF promoter; whereas RTEF-1 isoforms 669, 651, and 366 display an inhibitory effect.

Note that lumens measured in the no insert control (pcDNA plasmid w/o RTEF-1+pSEAP plasmid) are due to the endogenous activity on the exogenous VEGF promoter. Thus, any cotransfections with RTEF-1 isoforms that result in measured lumens below this value are believed to be the result of RTEF-1 isoforms interacting with endogenous cofactors necessary for VEGF transcriptional activity.

Results

Figure 2A:
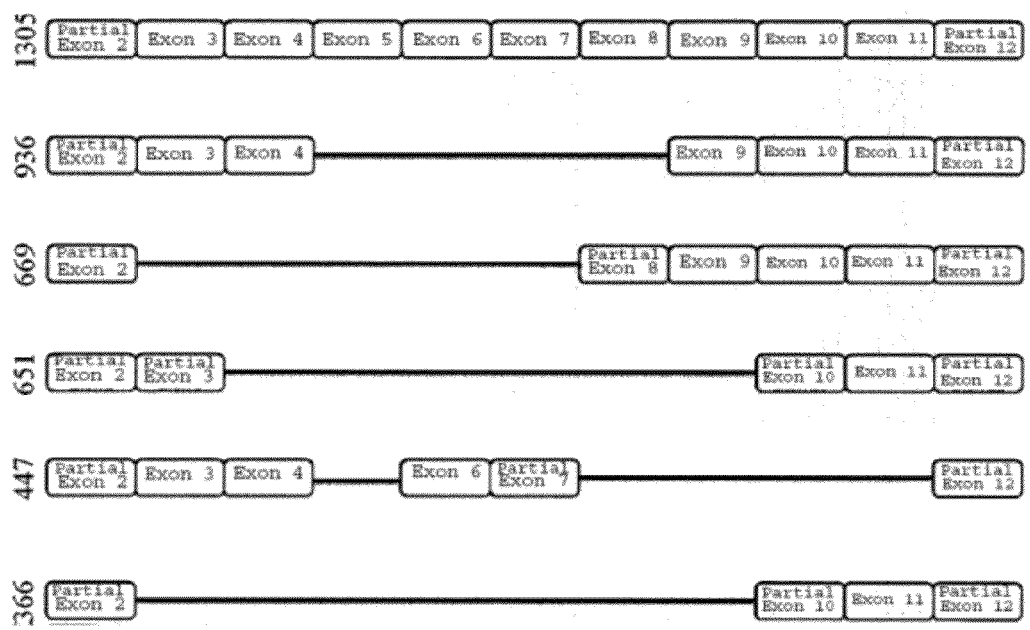

FIG. 2A-2C depict a schematic diagram of various RTEF isoforms. The 669 bp variant RTEF-1 and the 366 bp variant RTEF-1 isoform are depicted in FIG. 2E. As can be seen in FIG. 1, the 669 bp variant RTEF-1 and the 366 bp variant RTEF-1 isoform demonstrated significantly reduced VEGF promoter activity under hypoxic and normoxic conditions compared to other RTEF-1 isoforms that were tested. A p-value of less than 0.05 is indicative of a statistically significant difference.

In contrast to the RTEF-1 1305, 936, 651, and 447 isoforms that were harvested from retinal endothelial cells, RTEF-1 366 and 669 isoforms were isolated from Mel 202 cells (human choroidal melanoma cells).

Under hypoxic conditions, all RTEF-1 isoforms are significantly different from the no insert control except for the 651 isoform. RTEF-1 isoforms 366 and 669 show no significant difference (see Table 3).

TABLE 3

Unpaired T-Test p - values: Measured Lumens between RTEF-1 isoforms under Hypoxic Conditions

| RTEF-1 Isoform | 1305 | 669 | 651 | 447 | 366 | No insert |
|---|---|---|---|---|---|---|
| 1305 | | | | | | |
| 669 | 0.0023 | | | | | |
| 651 | 0.0011 | 0.0182 | | | | |
| 447 | 0.0381 | 0.0137 | 0.0150 | | | |
| 366 | 0.0022 | 0.0877 | 0.0187 | 0.0138 | | |
| No insert | 0.0017 | 0.0065 | 0.1171 | 0.0157 | 0.0052 | |

Under normoxic conditions, all isoforms are significantly different from the no insert control except for the 651 isoform. RTEF-1 isoform 651 shows no significant difference from that of the 366 or 669 isoforms. This is thought to be due to the higher variation between triplicate samples in the 651 normoxic wells (see Table 4).

TABLE 2

| | 1305 | 669 | 651 | 447 | 366 | No insert |
|---|---|---|---|---|---|---|
| Normoxic Lumens | | | | | | |
| Avg. of Avgs. | 108185.37 | 4440.60 | 27590.20 | 308097.60 | 7835.20 | 34289.00 |
| SD | 24234.07 | 1251.01 | 12294.25 | 30271.97 | 137.65 | 1859.00 |
| Hypoxic Lumens | | | | | | |
| Avg. of Avgs. | 203921.27 | 8937.67 | 33275.07 | 453160.20 | 11343.00 | 42251.27 |
| SD | 16329.02 | 698.28 | 5937.96 | 91022.17 | 1472.96 | 4959.10 |
| Lumen Fold Change | | | | | | |
| Normoxic | 3.16 | 0.13 | 0.80 | 8.99 | 0.23 | 1.00 |
| Hypoxic | 4.83 | 0.21 | 0.79 | 10.73 | 0.27 | 1.00 |

TABLE 4

Unpaired T-Test p - values: Measured Lumens between RTEF-1 isoforms under Normoxic Conditions

| RTEF-1 Isoform | 1305 | 669 | 651 | 447 | 366 | No insert |
|---|---|---|---|---|---|---|
| 1305 | | | | | | |
| 669 | 0.0175 | | | | | |
| 651 | 0.0147 | 0.0811 | | | | |
| 447 | 0.0011 | 0.0033 | 0.0013 | | | |
| 366 | 0.0189 | 0.0410 | 0.1085 | 0.0034 | | |
| No insert | 0.0334 | 0.0001 | 0.4455 | 0.0039 | 0.0016 | |

When comparing RTEF-1 isoforms under hypoxic to normoxic conditions, RTEF-1 651, 447, 366, and the no insert control showed significant difference (Table 5).

TABLE 5

Measured Lumens between hypoxic and normoxic conditions for each RTEF-1 isoform

| RTEF-1 Isoform | 1305 | 669 | 651 | 447 | 366 | No insert |
|---|---|---|---|---|---|---|
| P - value | 0.0070 | 0.0109 | 0.5248 | 0.0980 | 0.0529 | 0.0946 |

Example 2

Expression of SRF, MAX, and YAP65 in Cell Lines

Materials and Methods

Hek293 cells were grown in 6-well plates with appropriate media to 80% confluency. The media was removed and the cells were washed with PBS. Cellular RNA was isolated using the RNAquous-4 PCR kit (Ambion®). Briefly, 300 µl of lysis buffer was added to the cells and incubated for 5 minutes at room temperature. The lysate was collected and an equal volume of 65% ethanol was added and mixed by inversion. The mixture was passed through an RNA collection filter by centrifugation at 12,000 rpm and washed three times with wash buffer (Ambion®) by centrifugation at 12,000 rpm. Filters were centrifuged once more to completely dry the filter. Elution buffer (Ambion®) heated to 75° C. was added to the column and centrifuged to elute the RNA. RNA was quantified by a UV spectrophotometer using a 260 nm wavelength. Total RNA at a concentration of 250 ng was used for reverse transcription using the Omni-script RT kit (Qiagen). The reaction was composed of 2 µl of 10× RT buffer, 2 µl of dNTP mix (5 mM each dNTP), 2 µl of oligo-dT primer (10 µM), 1 µl of RNAse inhibitor (10 U/µl), 1 µl of reverse transcriptase and water. Reactions were incubated at 37° C. for one hour. The resulting cDNA was then used for PCR. The reaction was composed of 2 µl of the cDNA mixed with 2.5 µl of 10× buffer, 0.2 mM dNTPs, 20 pmols of the forward primer (5'tgtttcagccgcagcctctc3'; SEQ ID NO:21) and 20 pmols of reverse primer (5'tgggggctgcttcactgg3'; SEQ ID NO:22), 1 µl of RedTaq® and water. Reactions were incubated at 95° C. for 5 minutes with 35 cycles of 95° C. for 25 seconds, 55° C. for 20 seconds and 72° C. for 45 seconds, then 72° C. for 5 minutes. The PCR reactions were run out on a 1.5% agarose gel, visualized with ethidium bromide and photographed using an integrating camera.

Results

Results are shown in FIG. 4. All cell lines tested showed expression of SRF (lanes 1, 5 and 10) and Max (lanes 2, 6 and 11) and YAP65 (lanes 4, 8 and 13). The TAZ message is not amplifiable from RPE cells (lane 7) but is present in RVEC (lane 3) and 293T cells (lane 13).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,376,110
U.S. Pat. No. 4,554,101
U.S. Pat. No. 4,683,202
U.S. Pat. No. 4,684,611
U.S. Pat. No. 4,797,368
U.S. Pat. No. 4,816,567
U.S. Pat. No. 4,952,500
U.S. Pat. No. 5,139,941
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,136
U.S. Pat. No. 5,994,624
U.S. Pat. No. 6,013,516
U.S. Pat. No. 7,122,181
U.S. Appln. 20030008374
U.S. Appln. 20030082789
U.S. Appln. 2004005647
U.S. Appln. 20050175591
U.S. Appln. 20060171919
U.S. Appln. 20060223114
U.S. Appln. 20060234299

U.S. patent Ser. No. 07/715,272
U.S. patent Ser. No. 07/934,373
Almendro et al., *J. Immunol.*, 157(12):5411-5421, 1996.
Ausubel et al., In: *Current Protocols in Molecular Biology*, John, Wiley & Sons, Inc, NY, 1994.
Baichwal and Sugden, In: *Gene Transfer*, Kucherlapati (Ed.), Plenum Press, NY, 117-148, 1986.
Blomer et al., *J. Virol.*, 71(9):6641-6649, 1997.
Brodeur et al., In: *Monoclonal antibody production techniques and applications*, Marcel Dekker, Inc., NY, 51-63, 1987.
Carbonelli et al., *FEMS Microbiol. Lett.*, 177(1):75-82, 1999.
Chandler et al., *Proc. Natl. Acad. Sci. USA*, 94(8):3596-601, 1997.
Chen et al., *Genes & Dev.*, 24:290-300, 2010.
Chen and Okayama, *Mol. Cell Biol.*, 7(8):2745-2752, 1987.
Clackson et al., *Nature* 352: 624-628, 1991.
Cocea, *Biotechniques*, 23(5):814-816, 1997.
Cotten et al., *Proc. Natl. Acad. Sci. USA*, 89(13):6094-6098, 1992.
Coupar et al., *Gene*, 68:1-10, 1988.
Curiel, *Nat. Immun.*, 13(2-3):141-164, 1994.
David et al., *Biochemistry*, 13:1014, 1974.
Donahue et al., *Curr. Eye Res.*, 15:175-84, 1996.
Farrance et al., *J. Biol. Chem.*, 271:8266-74, 1996.
Fechheimer, et al., *Proc Natl. Acad. Sci. USA*, 84:8463-8467, 1987.
Fraley et al., *Proc. Natl. Acad. Sci. USA*, 76:3348-3352, 1979.
Friedmann, *Science*, 244:1275-1281, 1989.
Frigerio et al., *Hum. Mol. Genet.*, 4:37-43, 1995.
Goding, In: *Monoclonal Antibodies: Principles and Practice*, 2d ed., Academic Press, Orlando, Fla., pp 60-61, 71-74, 1986.
Gopal, *Mol. Cell Biol.*, 5:1188-1190, 1985.
Gragoudas et al., *N. Engl. J. Med.*, 351:2805-2816, 2004.
Graham and Van Der Eb, *Virology*, 52:456-467, 1973.
Griffith et al., *EMBO J.*, 12:725-734, 1993.
Grunhaus and Horwitz, *Seminar in Virology*, 3:237-252, 1992.
Harland and Weintraub, *J. Cell Biol.*, 101(3):1094-1099, 1985.
Horwich et al. *J. Virol.*, 64:642-650, 1990.
Hunter et al., *Nature*, 144:945, 1962.
Inouye and Inouye, *Nucleic Acids Res.*, 13:3101-3109, 1985.
Jakobovits et al., *Nature*, 362:255-258, 1993.
Jakobovits et al., *Proc. Natl. Acad. Sci. USA*, 90:2551-255, 1993.
Jiang et al., *Biochemistry*, 39:3505-13, 2000.
Johnson et al., In: *Biotechnology and Pharmacy*, Pezzuto et al., eds., Chapman and Hall, New York, 1993.
Jones et al., *Nature*, 321:522-525, 1986.
Kaeppler et al., *Plant Cell Reports*, 9:415-418, 1990.
Kanda et al., *Endothelium*, 6:33-44, 1998.
Kaneda et al., *Science*, 243:375-378, 1989.
Kaneko & DePamphilis, *Dev Genet*, 22:43-55, 1998.
Kato et al, *J. Biol. Chem.*, 266:3361-3364, 1991.
Kelleher and Vos, *Biotechniques*, 17(6):1110-7, 1994.
Kohler and Milstein, *Nature*, 256:495-497, 1975.
Kozbor, *J. Immunol.*, 133(6):3001-3005, 1984.
Kraus et al. *FEBS Lett.*, 428(3):165-170, 1998.
Lareyre et al., *J. Biol. Chem.*, 274(12):8282-8290, 1999.
Lashkari et al., *Am. J. Pathol.*, 156:1337-44, 2000.
Laughlin et al., *J. Virol.*, 60(2):515-524, 1986.
Lebkowski et al., *Mol. Cell. Biol.*, 8(10):3988-3996, 1988.
Lee et al., *Biochem. Biophys. Res. Commun.*, 238(2):462-467, 1997.
Levenson et al., *Hum. Gene Ther.*, 9(8):1233-1236, 1998.
Li et al., *Genes & Dev.*, 24:235-240, 2010.
Macejak and Sarnow, *Nature*, 353:90-94, 1991.
Maniatis, et al., *Molecular Cloning, A Laboratory Manual*, Cold Spring Harbor Press, Cold Spring Harbor, N.Y., 1988.
Mann et al., *Cell*, 33:153-159, 1983.
Marks et al., *Bio/Technol.*, 10:779-783, 1992.
Marks et al., *J. Mol. Biol.*, 222:581-97, 1991.
McCafferty et al., *Nature*, 348:552-553, 1990.
McLaughlin et al., *J. Virol.*, 62(6):1963-1973, 1988.
Miller et al., *Am. J. Clin. Oncol.*, 15(3):216-221, 1992.
Miller, *Am. J. Pathol.*, 151:13-23, 1997.
Morrison et al., *Proc. Natl. Acad. Sci. USA*, 81(21):6851-6855, 1984.
Munson and Pollard, *Anal. Biochem.*, 107:220, 1980.
Muzyczka, *Curr. Topics Microbiol. Immunol.*, 158:97-129, 1992.
Nabel et al., *Science*, 244(4910):1342-1344, 1989.
Naldini et al., *Science*, 272(5259):263-267, 1996.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nishioka et al., *Dev. Cell*, 16:398-410, 2009.
Nomoto et al., *Gene*, 236(2):259-271, 1999.
Nygren, *J. Histochem. Cytochem.*, 30(5):407-412, 1982.
Omirulleh et al., *Plant Mol. Biol.*, 21(3):415-428, 1993.
Onda et al., *Cancer Res.*, 64:1419-1424, 2004.
Orsulic et al., *J. Cell Sci.*, 112:1237-1245, 1999.
Ota and Sasaki, *Developement*, 135:4059-4069, 2008.
Overholtzer et al., *Cell Bio.*, 103(33):12405-12410, 2006.
Pain et al., *J. Immunol. Meth.*, 40:219, 1981.
Paskind et al., *Virology*, 67:242-248, 1975.
PCT Appln. WO 93/06213
PCT Appln. WO 94/09699
PCT Appln. WO 95/06128
Pe'er et al., *Lab. Invest.*, 72:638-45, 1995.
Pelletier and Sonenberg, *Nature*, 334(6180):320-325, 1988.
Pierce et al., *Arch. Ophthalmol.*, 114:1219-28, 1996.
Potrykus et al., *Mol. Gen. Genet.*, 199(2):169-177, 1985.
Potter et al., *Proc. Natl. Acad. Sci. USA*, 81:7161-7165, 1984.
Remington's Pharmaceutical Sciences, 18th Ed. Mack Printing Company, pp. 1289-1329, 1990.
Ridgeway, In: *Vectors: A Survey of Molecular Cloning Vectors and Their Uses*, Rodriguez et al. (Eds.), Stoneham: Butterworth, 467-492, 1988.
Riechmann et al., *Nature*, 332(6162):323-327, 1988.
Rippe, et al., *Mol. Cell Biol.*, 10:689-695, 1990.
Rothbard et al., *Nat. Medicine*, 6(11):1253-7, 2000.
Roux et. al., 1989
Sambrook et al., In: *Molecular cloning: a laboratory manual*, $2^{nd}$ Ed., Cold Spring Harbor Laboratory Press, Cold Spring Harbor, N.Y., 1989.
Semb and Christofori, *Am. J. Hum. Genet.*, 63:1588-1593, 1998.
Shie et al., *J. Biol. Chem.*, 279:25010-6, 2004.
Silverman et al., *Microvasc. Res.*, 70:32-42, 2005.
Steinhardt et al., *Human Pathology*, vol. 39, 11:1582-1589, 2008.
Stewart et al., *Genomics*, 37:68-76, 1996.
Temin, In: *Gene Transfer*, Kucherlapati (Ed.), NY, Plenum Press, 149-188, 1986.
Tratschin et al., *Mol. Cell. Biol.*, 4:2072-2081, 1984.
Tsumaki et al., *J. Biol. Chem.*, 273(36):22861-22864, 1998.
Tur-Kaspa et al., *Mol. Cell Biol.*, 6:716-718, 1986.
Vannay et al., *Pediatr. Res.*, 57:396-8, 2005.

Vassilev et al., *Genes Dev.*, 15:1229-1241, 2001.
Verhoeyen et al., *Science*, 239(4847):1534-1536, 1988.
von Minckwitz et al., *Breast Cancer Res.*, 7:R616-626, 2005.
Wang et al., *Cancer Sci.*, DOI: 10.1111/j.1349-7006.2010.01511.x
Waterhouse et al., *Nucl. Acids Res.*, 21:2265-2266, 1993.
Wilson et al., *Science*, 244:1344-1346, 1989.
Winthrop et al., *Clin. Cancer Res.*, 9:3845s-3853s, 2003.
Wong et al., *Gene*, 10:87-94, 1980.
Wright et al., *Curr. Protein Pept. Sci.*, 4(2):105-24, 2003.
Wu and Wu, *Biochemistry*, 27: 887-892, 1988.
Wu and Wu, *J. Biol. Chem.*, 262:4429-4432, 1987.
Wu et al., *Biochem. Biophys. Res. Commun.*, 233(1):221-226, 1997.
Yasunami et. al., *Biochem. Biophys. Res. Commun.*, 228:365-70, 1996.
Yockey et al., *J. Biol. Chem.*, 271:3727-36, 1996.
Young et al., *J. Aapos.* 1:105-10, 1997.
Zeng and Hong, *Cancer Cell*, 13:188-192, 2008. Zhao et al., *Genes Dev.*, 22:1962-1971, 2008.
Zhao-Emonet et al., *Biochim. Biophys. Acta*, 1442(2-3):109-119, 1998.
Zola, *In: Monoclonal Antibodies: A Manual of Techniques*, CRC Press, Inc., 147-158, 1987.
Zufferey et al., *Nat. Biotechnol.*, 15(9):871-875, 1997.
Zuzarte et al., *Biochim. Biophys. Acta.*, 1517:82-90, 2000.

What is claimed is:

1. An isolated variant RTEF-1 polypeptide that reduces VEGF promoter activity comprising an amino acid sequence that is at least 95% identical to the contiguous amino acids of 1) amino acids 24 to 47 of SEQ ID NO:15 and 2) each of SEQ ID NOs:16 and 17, but does not comprise the contiguous amino acids of SEQ ID NOs:8, 9, 11, and 12, further wherein said polypeptide does not include an amino acid sequence consisting of amino acids 1-16 of SEQ ID NO:8.

2. The isolated variant RTEF-1 polypeptide of claim 1, comprising an amino acid sequence that is at least 97% identical to the contiguous amino acids of 1) amino acids 24 to 47 of SEQ ID NO:15 and 2) each of SEQ ID NOs:16 and 17.

3. The isolated variant RTEF-1 polypeptide of claim 1, comprising an amino acid sequence that is at least 99% identical to the contiguous amino acids of 1) amino acids 24 to 47 of SEQ ID NO:15 and 2) each of SEQ ID NOs:16 and 17.

4. The isolated variant RTEF-1 polypeptide of claim 1, wherein the polypeptide is at least 95% identical to SEQ ID NO:1.

5. The isolated RTEF-1 polypeptide of claim 4, wherein the polypeptide is at least 97% identical to SEQ ID NO:1.

6. The isolated RTEF-1 polypeptide of claim 5, wherein the polypeptide is at least 99% identical to SEQ ID NO:1.

7. The isolated RTEF-1 polypeptide of claim 6, wherein the polypeptide comprises SEQ ID NO:1.

8. The isolated RTEF-1 polypeptide of claim 1, wherein the polypeptide is at least 95% identical to SEQ ID NO:2.

9. The isolated RTEF-1 polypeptide of claim 8, wherein the polypeptide is at least 97% identical to SEQ ID NO:2.

10. The isolated RTEF-1 polypeptide of claim 8, wherein the polypeptide is at least 99% identical to SEQ ID NO:2.

11. The isolated RTEF-1 polypeptide of claim 10, wherein the RTEF-1 polypeptide comprises SEQ ID NO:2.

12. The isolated RTEF-1 polypeptide of claim 1, further comprising a cell internalization moiety or a nuclear localization sequence that is a polypeptide, an antibody, an aptamer or an avimer.

13. The isolated RTEF-1 polypeptide of claim 12, wherein the cell internalization moiety is a polypeptide comprising an HIV tat polypeptide, HSV-1 tegument protein VP22, or *Drosophila* antennopedia protein.

14. The isolated RTEF-1 polypeptide of claim 12, wherein the cell internalization moiety is a polypeptide comprising poly-arginine, poly-methionine or poly-glycine.

15. The isolated RTEF-1 polypeptide of claim 12, wherein the cell internalization moiety is a polypeptide comprising RMRRMRRMRR (SEQ ID NO:20).

16. The isolated RTEF-1 polypeptide of claim 12, wherein the cell internalization moiety is an antibody that is an IgA, an IgM, an IgE, an IgG, a Fab, a F(ab')2, a single chain antibody or a paratope peptide.

17. The isolated RTEF-1 polypeptide of claim 1, further comprising a cell secretion signal.

18. The isolated RTEF-1 polypeptide of claim 17, wherein the cell secretion signal comprises the human IL-2 secretion signal sequence (SEQ ID NO:23).

19. A kit comprising a predetermined quantity of a variant RTEF-1 polypeptide of claim 1 in one or more sealed vials.

20. A pharmaceutical composition comprising a) one or more variant RTEF-1 polypeptides as set forth in claim 1; and b) a pharmaceutically acceptable carrier.

21. The pharmaceutical composition of claim 20, comprising SEQ ID NO:1 or SEQ ID NO:2.

22. A method of inducing cell contact inhibition in a population comprising two or more cells, comprising contacting a cell of the population with an effective amount of a variant RTEF-1 polypeptide of claim 1, wherein cell contact inhibition in the population is induced.

23. A method of suppressing YAP activity in a cell, comprising contacting a cell with an effective amount of a variant RTEF-1 polypeptide of claim 1, wherein YAP activity in the cell is suppressed.

24. The method of claim 23, wherein the cell is contacted with a variant RTEF-1 polypeptide comprising a nuclear localization sequence and activity of YAP in the nucleus of the cell is suppressed.

25. The method of claim 23, wherein the variant RTEF-1 polypeptide does not include a nuclear localization sequence and wherein translocation of YAP into the nucleus of the cell is inhibited.

26. A method for treating a subject with a disorder associated with abnormal cell growth or abnormal cell proliferation, comprising administering to a subject with a disorder associated with abnormal cell growth or abnormal cell proliferation an effective amount of a pharmaceutical composition comprising a variant RTEF-1 polypeptide according to claim 1: wherein the disorder is treated.

27. The method of claim 26, wherein the disorder associated with abnormal cell growth or abnormal cell proliferation is an angiogenic disorder that is cancer, ocular neovascularization, an arterio-venous malformation, coronary restenosis, peripheral vessel restenosis, glomerulonephritis, or rheumatoid arthritis.

28. The method of claim 26, wherein the angiogenic disorder is cancer.

29. The method of claim 28, wherein the cancer is a cancer selected from the group consisting of cancer of breast cancer, lung cancer, prostate cancer, leukemia, lymphoma, head and neck cancer, brain cancer, stomach cancer, intestinal cancer, colorectal cancer, renal cancer, bladder cancer, testicular cancer, esophageal cancer, ocular melanoma, retinoblastoma, liver cancer, ovarian cancer, skin cancer, cancer of the tongue, cancer of the mouth, or metastatic cancer.

30. The method of claim 28, wherein the cancer is comprised of cancer cells that demonstrate detectable YAP in the nucleus and/or cytoplasm.

31. The method of claim 28, wherein the cancer cells demonstrate overexpression of YAP in the nucleus and/or cytoplasm compared to expression of YAP in the nucleus and/or cytoplasm of a cell of a similar tissue type that is not cancerous.

32. The method of claim 27, wherein the angiogenic disorder is ocular neovascularization.

33. The method of claim 32, wherein the ocular neovascularization is neovascularization due to age-related macular degeneration, neovascularization due to corneal graft rejection, neovascularization due to retinopathy of prematurity (ROP), or neovascularization due to diabetic retinopathy.

34. The method of claim 27, further comprising administering a secondary therapy for treatment of the antiangiogenic disorder.

35. The method of claim 34, wherein the secondary therapy is an antibody that binds to VEGF, a VEGF receptor, FGF, an FGF receptor, bevacizumab, ranibizumab, or pegaptanib sodium.

36. The method of 34, wherein the secondary therapy is an anticancer therapy that is chemotherapy, surgical therapy, immunotherapy or radiation therapy.

37. The method of claim 26, wherein the subject is a human.

38. The method of claim 26, wherein the composition is administered intravenously, intraarterially, epidurally, intrathecally, intraperitoneally, subcutaneously, orally, or topically.

39. The method of claim 32, wherein the composition is administered locally to the eye by topical drops, intracameral injection, subconjunctival injection, subtenon injection, or by intravitreous injection.

\* \* \* \* \*

UNITED STATES PATENT AND TRADEMARK OFFICE
CERTIFICATE OF CORRECTION

PATENT NO. : 8,785,385 B2  Page 1 of 1
APPLICATION NO. : 13/089687
DATED : July 22, 2014
INVENTOR(S) : J. Timothy Stout et al.

It is certified that error appears in the above-identified patent and that said Letters Patent is hereby corrected as shown below:

Title page, item (56) References Cited - Other Publications, delete the 2nd reference on page 1 "Benottehan and Colombo, "Anti-angiogenic strategies for cancer therapy (Review)," *International Journal of Oncology*, 27:563-574, 2005." and replace with --Benouchan and Colombo, "Anti-angiogenic strategies for cancer therapy (Review)," *International Journal of Oncology*, 27:563-574, 2005.-- therefor.

Title page, item (56) References Cited - Other Publications, delete the 15th reference on page 2 "Shimizu et al. "Antinoevascular therapy, a novel antiangiogenic approach," *Expert Opin. Ther. Targets*, 9(1):63-76. 2005." and replace with --Shimizu et al., "Antineovascular therapy, a novel antiangiogenic approach," *Expert Opin. Ther. Targets*, 9(1):63-76, 2005.-- therefor.

Title page, item (56) References Cited - Other Publications, delete the 21st reference on page 2 "Unirprot: "Sequence UPI0000E001FC," Sep. 13. 2006, XP55022838, Retrieved from the Internet: www.uniprot.org/uniparc/UPI0000E001FC, retrieved on Mar. 26, 2012." and replace with --Uniprot: "Sequence UPI0000E001FC," Sep. 13, 2006, XP55022838, Retrieved from the Internet: www.uniprot.org/uniparc/ UPI0000E001FC, retrieved on Mar. 26, 2012.-- therefor.

Title page, item (56) References Cited - Other Publications, delete the 25th reference on page 2 "Winthrop et al., "Selection and characterization or anti-MUC-1 scFvs intended for targeted therapy," *Clin. Cancer Res.*, 9 (10 pt. 2): 3845s-3853s, 2003." and replace with --Winthrop et al., "Selection and characterization of anti-MUC-1 scFvs intended for targeted therapy," *Clin. Cancer Res.*, 9 (10 pt. 2): 3845s-3853s, 2003.-- therefor.

In the Claims

In claim 26, column 56, line 21, delete "claim 1:" and replace with --claim 1,-- therefor.

In claim 36, column 56, line 63, delete "of 34," and replace with --of claim 34,-- therefor.

Signed and Sealed this
Eleventh Day of November, 2014

Michelle K. Lee
*Deputy Director of the United States Patent and Trademark Office*